(12) United States Patent
Hirakawa et al.

(10) Patent No.: US 7,951,569 B2
(45) Date of Patent: May 31, 2011

(54) THERMOSTABLE DUPLEX-SPECIFIC NUCLEASE

(75) Inventors: Yuzo Hirakawa, Hiroshima (JP); Isao Ohiso, Hiroshima (JP)

(73) Assignee: Nishikawa Rubber Co., Ltd., Hiroshima-shi (JP)

( * ) Notice: Subject to any disclaimer, the term of this patent is extended or adjusted under 35 U.S.C. 154(b) by 0 days.

(21) Appl. No.: 12/552,896

(22) Filed: Sep. 2, 2009

(65) Prior Publication Data
US 2010/0092976 A1    Apr. 15, 2010

(30) Foreign Application Priority Data

Sep. 3, 2008 (JP) ................................. 2008-226389
Jun. 1, 2009 (JP) ................................. 2009-131942

(51) Int. Cl.
C12N 9/00 (2006.01)
C12N 9/16 (2006.01)
C12N 1/20 (2006.01)
C12N 15/00 (2006.01)
C07H 21/04 (2006.01)

(52) U.S. Cl. ..................... 435/196; 435/183; 435/252.3; 435/320.1; 536/23.2

(58) Field of Classification Search ........................ None
See application file for complete search history.

(56) References Cited

U.S. PATENT DOCUMENTS
2005/0164216 A1    7/2005 Lukyanov et al.

OTHER PUBLICATIONS

Chica et al. Curr Opin Biotechnol. Aug. 2005;16(4):378-84.*
Sen et al. Appl Biochem Biotechnol. Dec. 2007;143(3):212-23.*
Veronika E. Anisimova, et al. "Is crab duplex-specific nuclease a member of the *Serratia* family of non-specific nucleases?", GENE, vol. 418, No. 1-2, XP22716638A, Jul. 15, 2008, pp. 41-48.
Veronika E. Anisimova, et al., "Isolation, characterization and molecular cloning of Duplex-Specific Nuclease from the hepatopancreas of the Kamchatka crab", BMC Biochemistry, vol. 9, No. 14, XP002555506, May 21, 2008, pp. 1-12.
Dmitry A. Shagin, et al., "A Novel Method for SNP Detection Using a New Duplex-Specific Nuclease From Crab Hepatopancreas", Genome Research, vol. 12, No. 12, XP002555507, Dec. 2002, pp. 1935-1942.
Pavel A. Zhulidov, et al., "Simple cDNA normalization using kamchatka crab duplex-specific nuclease", Nucleic Acids Research, vol. 32, No. 3, XP002555508, Feb. 18, 2004, pp. 1-8.
V.E. Anisimova, et al., "Renaturation, Activation, and Practical Use of Recombinant Duplex-Specific Nuclease from Kamchatka Crab", Biochemistry (Moscow), vol. 71, No. 5, XP002555510, May 2006, pp. 513-519.
Veronika E. Anisimova, et al., "Thermolabile duplex-specific nuclease" Biotechnology Letters, vol. 31, No. 2, XP002555509, Sep. 23, 2008. pp. 251-257.
Office Action issued Oct. 25, 2010, in European Patent Application No. 09 169 259.0.

* cited by examiner

*Primary Examiner* — Christian L Fronda
(74) *Attorney, Agent, or Firm* — Oblon, Spivak, McClelland, Maier & Neustadt, L.L.P.

(57) ABSTRACT

The present invention provides a thermostable duplex-specific nuclease (DSN) and a method for digesting a nucleic acid using said DSN, namely, a protein having a Brachyura-derived duplex-specific nuclease activity, a gene encoding for said protein, a recombinant vector comprising said gene and a transformed cell or transduced cell comprising said vector and a method for producing a protein having a duplex-specific nuclease activity, which comprises culturing said transformed cell or transduced cell using a medium and collecting the protein having a duplex-specific nuclease activity from the cultured mixture, a method for digesting a nucleic acid using said protein having duplex-specific nuclease activity, a method for detecting RNA using said DSN and a reagent kit to be used in the aforementioned methods.

24 Claims, 12 Drawing Sheets

Fig. 2

SEQUENCE LISTING

```
<160> NUMBER OF SEQ ID NOS: 28

<210> SEQ ID NO 1
<211> LENGTH: 1215
<212> TYPE: DNA
<213> ORGANISM: Chionoecetes opilio

<400> SEQUENCE: 1
atggagcctg ggcgagtact ctccacgaac tttattctag tcggtctgct ctccgcatat      60
gcctacagtt cggactgcgt gtggaacagg gactcggact ttcctgtgta ctcgccgctc     120
atcctcgact cctctttcga cttcgtgctg ccggtggagg aggatggcaa caagatagtt     180
```

```
aggatagcgg cgggagccac cgtgactttg gcatgtccag gcaacgagat agcgagtctt    240
catcaggtag aggcagaggc tcgctgcctc gacaacggcc tcctggcaat cgataattcc    300
gagtgggact tggcgagtct gggctgcgcg cggcccgtga aggagacgat tttccgcgac    360
ctgggaacat gtggcgccga ggacatcgga acccttcatg cgatcggctt cgagattgtc    420
agtctgggca aatacaagga gatcattcgt gtgtgcttcg agccttcctc cgagacgacc    480
ctcttcaccg agcacgtcat tcacggcgcc aacatcgctg ccaaggacat cgacacgtca    540
aggccatcct tcaggacctc ctcggggttt ttcagcattt ccatgatcaa agcttactct    600
caaagttcac agctagtgct catgacaaat cttcttggcg atgaggacct tgccctctca    660
gtcattgaca tacacaaaca actctacttc gccaaaggcc acatgtcccc agacgccgac    720
ttcgtgttga tggcaaacca ggatgcttct tactactaca tcaacgcctt accacagtgg    780
caggtattca acaacgggaa ctggaggaac ttggagtacg ccactcggga tctggcggag    840
aagaaagggc gtgacctgcg ggtgattagt gggggttggg gtattctgga gctaaacgac    900
attaacggca accccgtaga gatattcctg gggctgatag atgacaagaa agttgtaccc    960
gcgccagcaa tcacgtggaa ggtggtgtat gatgagtcaa ctaactgcgc gcggctgtc    1020 gtgggcgtca caacccatt cctcaccacc gcccccagga agctttgcga ggacctctgc    1080
tcctcactct cctggataga cttcgatgtg ggtgacctgg cgcacggcta cacctactgc    1140
tgctccgtga aggacttgcg agcctccgtg ccccatgttc ccgacctcgg tgatgtttgt    1200
cttctcactg attga                                                    1215
```

<210> SEQ ID NO 2
<211> LENGTH: 404
<212> TYPE: PRT
<213> ORGANISM: Chionoecetes opilio

<400> SEQUENCE: 2

```
Met Glu Pro Gly Arg Val Leu Ser Thr Asn Phe Ile Leu Val Gly Leu
1               5                   10                  15

Leu Ser Ala Tyr Ala Tyr Ser Ser Asp Cys Val Trp Asn Arg Asp Ser
            20                  25                  30

Asp Phe Pro Val Tyr Ser Pro Leu Ile Leu Asp Ser Ser Phe Asp Phe
        35                  40                  45

Val Leu Pro Val Glu Glu Asp Gly Asn Lys Ile Val Arg Ile Ala Ala
    50                  55                  60

Gly Ala Thr Val Thr Leu Ala Cys Pro Gly Asn Glu Ile Ala Ser Leu
65                  70                  75                  80

His Gln Val Glu Ala Glu Ala Arg Cys Leu Asp Asn Gly Leu Leu Ala
                85                  90                  95

Ile Asp Asn Ser Glu Trp Asp Leu Ala Ser Leu Gly Cys Ala Arg Pro
            100                 105                 110

Val Lys Glu Thr Ile Phe Arg Asp Leu Gly Thr Cys Gly Ala Glu Asp
        115                 120                 125

Ile Gly Thr Leu His Ala Ile Gly Phe Glu Ile Val Ser Leu Gly Lys
    130                 135                 140

Tyr Lys Glu Ile Ile Arg Val Cys Phe Glu Pro Ser Ser Glu Thr Thr
145                 150                 155                 160

Leu Phe Thr Glu His Val Ile His Gly Ala Asn Ile Ala Ala Lys Asp
                165                 170                 175

Ile Asp Thr Ser Arg Pro Ser Phe Arg Thr Ser Ser Gly Phe Phe Ser
            180                 185                 190
```

```
Ile Ser Met Ile Lys Ala Tyr Ser Gln Ser Gln Leu Val Leu Met
        195                 200                 205
Thr Asn Leu Leu Gly Asp Glu Asp Leu Ala Leu Ser Val Ile Asp Ile
210                 215                 220
His Lys Gln Leu Tyr Phe Ala Lys Gly His Met Ser Pro Asp Ala Asp
225                 230                 235                 240
Phe Val Leu Met Ala Asn Gln Asp Ala Ser Tyr Tyr Tyr Ile Asn Ala
                245                 250                 255
Leu Pro Gln Trp Gln Val Phe Asn Asn Gly Asn Trp Arg Asn Leu Glu
            260                 265                 270
Tyr Ala Thr Arg Asp Leu Ala Glu Lys Lys Gly Arg Asp Leu Arg Val
        275                 280                 285
Ile Ser Gly Gly Trp Gly Ile Leu Glu Leu Asn Asp Ile Asn Gly Asn
    290                 295                 300
Pro Val Glu Ile Phe Leu Gly Leu Ile Asp Asp Lys Lys Val Val Pro
305                 310                 315                 320
Ala Pro Ala Ile Thr Trp Lys Val Val Tyr Asp Glu Ser Thr Asn Cys
                325                 330                 335
Ala Ala Ala Val Val Gly Val Asn Asn Pro Phe Leu Thr Thr Ala Pro
            340                 345                 350
Arg Lys Leu Cys Glu Asp Leu Cys Ser Ser Leu Ser Trp Ile Asp Phe
        355                 360                 365
Asp Val Gly Asp Leu Ala His Gly Tyr Thr Tyr Cys Cys Ser Val Lys
    370                 375                 380
Asp Leu Arg Ala Ser Val Pro His Val Pro Asp Leu Gly Asp Val Cys
385                 390                 395                 400
Leu Leu Thr Asp

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
gccaacattg ccgccaagga                                                 20

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
gccaaggaca tcgagacctc                                                 20

<210> SEQ ID NO 5
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
ttcaagacct ccaccgggtt cttca                                           25
```

```
<210> SEQ ID NO 6
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
tgccattatt gaaggcctgc cactg                                          25

<210> SEQ ID NO 7
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
cttgccctct cagtcattga catac                                          25

<210> SEQ ID NO 8
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
atacacaaac aactctactt cgcc                                           24

<210> SEQ ID NO 9
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
gtttgtgtat gtcaatgact gagag                                          25

<210> SEQ ID NO 10
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
gcaaggtcct catcgccaag aag                                            23

<210> SEQ ID NO 11
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
gcactagctg tgaactttga gag                                            23
```

```
<210> SEQ ID NO 12
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
gagagaaaga ttggcgagag gga                                           23

<210> SEQ ID NO 13
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
ggaaagatct gggagtaaag agg                                           23

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
ggccacgcgt cgactagtac                                               20

<210> SEQ ID NO 15
<211> LENGTH: 36
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (24)..(25)
<223> OTHER INFORMATION: Inosine
<220> FEATURE:
<221> NAME/KEY: modified_base
<222> LOCATION: (29)..(30)
<223> OTHER INFORMATION: Inosine
<220> FEATURE:
<221> NAME/KEY: modified_base
<222> LOCATION: (34)..(35)
<223> OTHER INFORMATION: Inosine

<400> SEQUENCE: 15
ggccacgcgt cgactagtac gggnngggnn gggnng                             36

<210> SEQ ID NO 16
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
ggccacgcgt cgactagtac ttttttttt ttttttt                             37

<210> SEQ ID NO 17
<211> LENGTH: 20
<212> TYPE: DNA
```

<213> ORGANISM: Artificial Sequence
<220> FEATURE:
<223> OTHER INFORMATION: Description of Artificial Sequence: Synthetic
     primer

<400> SEQUENCE: 17
tttttttttt tttttttttt                                              20

<210> SEQ ID NO 18
<211> LENGTH: 35
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 18
aaggatccat ggagcctggg cgagtactct ccacg                             35

<210> SEQ ID NO 19
<211> LENGTH: 54
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 19
ccgaattctc aatgatgatg atgatgatga tcagtgagaa gacaaacatc accg        54

<210> SEQ ID NO 20
<211> LENGTH: 1293
<212> TYPE: DNA
<213> ORGANISM: Chionoecetes opilio

<400> SEQUENCE: 20
gagagaaaga ttggcgagag ggaagcagat gaaatggagc ctgggcgagt actctccacg    60
aactttattc tagtcggtct gctctccgca tatgcctaca gttcggactg cgtgtggaac   120
agggactcgg actttcctgt gtactcgccg ctcatcctcg actcctcttt cgacttcgtg   180
ctgccggtgg aggaggatgg caacaagata gttaggatag cggcgggagc caccgtgact   240
ttggcatgtc caggcaacga gatagcgagt cttcatcagg tagaggcaga ggctcgctgc   300
ctcgacaacg gcctcctggc aatcgataat tccgagtggg acttggcgag tctgggctgc   360
gcgcggcccg tgaaggagac gattttccgc gacctgggaa catgtggcgc cgaggacatc   420
ggaacccttc atgcgatcgg cttcgagatt gtcagtctgg gcaaatacaa ggagatcatt   480
cgtgtgtgct tcgagccttc ctccgagacg accctcttca ccgagcacgt cattcacggc   540
gccaacatcg ctgccaagga catcgacacg tcaaggccat ccttcaggac ctcctcgggg   600
tttttcagca tttccatgat caaagcttac tctcaaagtt cacagctagt gctcatgaca   660
aatcttcttg gcgatgagga ccttgccctc tcagtcattg acatacacaa acaactctac   720
ttcgccaaag gccacatgtc cccagacgcc gacttcgtgt tgatggcaaa ccaggatgct   780
tcttactact acatcaacgc cttaccacag tggcaggtat caacaacgg gaactggagg   840 aacttggagt acgccactcg ggatctggcg gagaagaaag ggcgtgacct gcgggtgatt   900
agtgggggtt ggggtattct ggagctaaac gacattaacg gcaaccccgt agagatattc   960
ctggggctga tagatgacaa gaaagttgta cccgcgccag caatcacgtg gaaggtggtg  1020
tatgatgagt caactaactg cgccgcggct gtcgtgggcg tcaacaaccc attcctcacc  1080 accgcccccca ggaagctttg cgaggacctc tgctcctcac tctcctggat agacttcgat  1140

```
gtgggtgacc tggcgcacgg ctacacctac tgctgctccg tgaaggactt gcgagcctcc    1200
gtgccccatg ttcccgacct cggtgatgtt tgtcttctca ctgattaacc tctttactcc    1260
cagatctttc ctttgctaaa aaaaaaaaaa aaa                                 1293
```

<210> SEQ ID NO 21
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 21

```
ttttttttttt tttttttttt ttttt                                           25
```

<210> SEQ ID NO 22
<211> LENGTH: 6
<212> TYPE: PRT
<213> ORGANISM: Artificial Sequence Sequence
<220> FEATURE:
<223> OTHER INFORMATION: Description of Artificial Sequence: Synthetic
      6xHis tag

<400> SEQUENCE: 22

```
His His His His His His
1               5
```

<210> SEQ ID NO 23
<211> LENGTH: 402
<212> TYPE: PRT
<213> ORGANISM: Penaeus japonicus

<400> SEQUENCE: 23

```
Met Ala Gly Phe Gly Leu Gln Ala Phe Phe Ile Val Thr Leu Leu Gly
1               5                   10                  15

Val Gly Val Thr Gly Gln Glu Cys Met Trp Asn Lys Asp Thr Asp Phe
            20                  25                  30

Pro Glu Tyr Pro Pro Ile Ile Leu Asp Ala Ser Leu Glu Ile Val Arg
        35                  40                  45

Pro Val Ala Glu Gly Gly Ala Arg Val Val Arg Val Ser Ala Gly Ala
    50                  55                  60

Lys Leu Thr Leu Ala Cys Pro Gly Ser Glu Ile Val Asn Leu Gly Thr
65                  70                  75                  80

Thr Ala Val Asp Val Gln Cys Gly Gly Gly Asn Leu Leu Val Val Asp
                85                  90                  95

Gly Thr Glu Trp Arg Met Asp Glu Leu Gly Cys Ser Lys Lys Asp Lys
            100                 105                 110

Glu Thr Ile His Arg Asn Leu Gly Ser Cys Gly Asp Gly Gly Val Gly
        115                 120                 125

Val Phe Glu Gly Ile Gly Phe Glu Ile Phe Gly Ser Asp Ser Phe Tyr
    130                 135                 140

Glu Leu Ile Arg Val Cys Phe Glu Pro Lys Ala Glu Thr Thr Leu Tyr
145                 150                 155                 160

Ser Glu His Val Leu His Gly Ala Asn Ile Ala Ala Lys Asp Ile Asp
                165                 170                 175

Ser Ser Arg Pro Ser Phe Lys Ser Ser Thr Gly Phe Phe Thr Val Ser
            180                 185                 190

Met Ser Thr Cys Tyr Thr Gln Asn Ser Gln Leu Ala Ser Met Lys Ile
        195                 200                 205
```

```
Leu Leu Gly Asp Asp Asp Leu Ala Asn Ala Ile Ile Asn Pro His Glu
    210                 215                 220
Gln Tyr Tyr Phe Ala Lys Gly His Met Ala Pro Asp Ala Asp Phe Val
225                 230                 235                 240
Thr Glu Ala Glu Gln Asp Ala Thr Tyr Tyr Ile Asn Ala Val Pro
                245                 250                 255
Gln Trp Gln Ala Phe Asn Asn Gly Asn Trp Lys Tyr Leu Glu Phe Ala
                260                 265                 270
Thr Arg Asp Leu Ala Glu Ser His Ser Thr Asp Leu Thr Ile Tyr Thr
                275                 280                 285
Gly Gly Trp Gly Leu Leu Thr Leu Asp Asp Ile Asn Gly Asn Pro Val
    290                 295                 300
Glu Ile Tyr Leu Gly Leu Thr Glu Asp Glu Met Val Val Pro Ala Pro
305                 310                 315                 320
Ala Ile Thr Trp Lys Val Val Tyr Glu Glu Ser Ser Ser Arg Ala Val
                325                 330                 335
Gly Val Val Gly Val Asn Asn Pro His Ile Thr Ser Pro Pro Thr Pro
                340                 345                 350
Leu Cys Ser Asp Leu Cys Ser Ser Leu Ala Trp Ile Asp Phe Asp Val
                355                 360                 365
Asn Asp Leu Gly His Gly Tyr Thr Tyr Cys Cys Thr Val Asp Asp Leu
    370                 375                 380
Arg Ala Ala Ile Pro His Val Pro Asp Leu Gly Ser Val Gly Leu Leu
385                 390                 395                 400
Asp Lys

<210> SEQ ID NO 24
<211> LENGTH: 407
<212> TYPE: PRT
<213> ORGANISM: Paralithodes camtschaticus

<400> SEQUENCE: 24

Met Ala Asn Met Glu Ser Lys Gln Gly Ile Met Val Leu Gly Phe Leu
1               5                   10                  15
Ile Val Leu Leu Phe Val Ser Val Asn Gly Gln Asp Cys Val Trp Asp
                20                  25                  30
Lys Asp Thr Asp Phe Pro Glu Asp Pro Pro Leu Ile Phe Asp Ser Asn
                35                  40                  45
Leu Glu Leu Ile Arg Pro Val Leu Glu Asn Glu Lys Arg Ile Val Ser
    50                  55                  60
Val Pro Ser Gly Ser Ser Leu Thr Leu Ala Cys Ser Gly Ser Glu Leu
65                  70                  75                  80
Ile Asn Leu Gly Met Glu Ala Val Glu Ala Lys Cys Ala Gly Gly Val
                85                  90                  95
Met Leu Ala Ile Glu Gly Thr Glu Trp Glu Ile Trp Ser Leu Gly Cys
                100                 105                 110
Ser Asn His Val Lys Glu Ser Ile Arg Arg Asn Leu Gly Thr Cys Gly
            115                 120                 125
Glu Ala Asp Gln Gly Asp Arg His Ser Ile Gly Phe Glu Tyr Tyr Gly
        130                 135                 140
Gly Ser Ile Tyr Tyr Glu Leu Ile Ser Val Cys Phe Glu Pro Val Ser
145                 150                 155                 160
Glu Thr Thr Leu Tyr Thr Glu His Val Leu His Gly Ala Asn Ile Ala
                165                 170                 175
```

```
Ala Lys Asp Ile Glu Thr Ser Arg Pro Ser Phe Lys Thr Ser Thr Gly
            180                 185                 190

Phe Phe Ser Val Ser Met Ser Thr Val Tyr Ser Gln Ala Ser Gln Leu
            195                 200                 205

Gln Leu Met Thr Asp Ile Leu Gly Asp Ser Asp Leu Ala Asn Asn Ile
    210                 215                 220

Ile Asp Pro Ser Gln Gln Leu Tyr Phe Ala Lys Gly His Leu Ser Pro
225                 230                 235                 240

Asp Ala Asp Phe Val Thr Val Ala Glu Gln Asp Ala Thr Tyr Tyr Phe
                245                 250                 255

Ile Asn Ala Leu Pro Gln Trp Gln Ala Phe Asn Asn Gly Asn Trp Lys
            260                 265                 270

Tyr Leu Glu Tyr Ala Thr Arg Asp Leu Ala Glu Ser His Gly Ser Asp
        275                 280                 285

Leu Arg Val Tyr Ser Gly Gly Trp Ser Val Leu Gln Leu Asp Asp Ile
    290                 295                 300

Asn Gly Asn Pro Val Asp Ile Leu Leu Gly Leu Ser Glu Gly Lys Glu
305                 310                 315                 320

Val Val Pro Val Pro Ser Leu Thr Trp Lys Val Val Tyr Glu Glu Ser
                325                 330                 335

Ser Ser Lys Ala Ala Ala Ile Val Gly Ile Asn Asn Pro His Ile Thr
            340                 345                 350

Thr Ala Pro Ser Pro Leu Cys Ser Asp Leu Cys Ser Ser Leu Thr Trp
        355                 360                 365

Ile Asp Phe Asn Leu Asp Asp Leu Ala His Gly Tyr Thr Tyr Cys Cys
    370                 375                 380

Ala Val Asp Asp Leu Arg Gln Ala Ile Pro Tyr Ile Pro Asp Leu Gly
385                 390                 395                 400

Asn Val Gly Leu Leu Thr Asn
                405

<210> SEQ ID NO 25
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
aaaaaaaaaa aaaaaaaaaa aaaaaaaaaa aaaaaaa                              37

<210> SEQ ID NO 26
<211> LENGTH: 10
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 26
tttttttttt                                                            10

<210> SEQ ID NO 27
<211> LENGTH: 12
<212> TYPE: DNA
<213> ORGANISM: Artificial Sequence
<220> FEATURE:
<223> OTHER INFORMATION: Description of Artificial Sequence: Synthetic
      probe
```

-continued

```
<400> SEQUENCE: 27
tttttttttt tt                                                          12

<210> SEQ ID NO 28
<211> LENGTH: 13
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 28
tttttttttt ttt                                                         13
```

THERMOSTABLE DUPLEX-SPECIFIC NUCLEASE

CROSS-REFERENCE TO RELATED APPLICATIONS

The present application claims priority to Japanese patent applications JP 2009-131942, filed on Jun. 1, 2009, and JP 2008-226389, filed on Sep. 3, 2008, which are incorporated herein by reference in their entireties.

BACKGROUND OF THE INVENTION

1. Field of the Invention

This invention relates to a thermostable double strand-specific nucleic acid degrading enzyme (nuclease) (duplex-specific nuclease: to be referred to as DSN hereinafter) and a gene of said enzyme. It also relates to a novel thermostable DSN which can be easily produced using a recombinant protein expression technique, and a method for producing said DSN. It also relates to a novel thermostable DSN derived from an organism belonging to Brachyura, more illustratively derived from an organism belonging to Majidae, further illustratively derived from the genus *Chionoecetes*. It further relates to a method for digesting nucleic acid using said DSN and a method for detecting RNA using said DSN, and a reagent kit to be used in the aforementioned methods.

2. Brief Description of the Background Art

Nucleases which show DNase (DNA degrading enzyme) activity have so far been found in the digestive gland or hepatopancreas of some crustaceans, particularly Decapoda such as shrimps, crabs and the like. Particularly, it has been revealed that a king crab liver-derived nuclease is a characteristic enzyme which shows a DNase activity highly specific to double-stranded nucleic acid, and this enzyme has been called as duplex-specific nuclease (DSN).

i) *Solenocera melantho* (a Mud Shrimp) DNase

A nuclease derived from Decapoda such as shrimps, crabs and the like was firstly purified from *Solenocera melantho* of the family Solenoceridae as a hepatopancreas-derived DNase (*Biochim Biophys Acta*, 1036, 95-100(1990)). The *Solenocera melantho* DNase had a molecular weight (about 44 kDa) which was larger than that of a bovine hepatopancreas-derived DNase. It was confirmed that the *Solenocera melantho* DNase does not have a sugar chain, and it was considered that its large molecular weight is due to its long polypeptide chain. Although the *Solenocera melantho* DNase had a metal ion requirement and optimum activity pH, which were close to those of a bovine pancreas-derived DNase, it did not show an RNase (RNA degrading enzyme) activity. In addition, it was shown that the *Solenocera melantho* DNase has a resistance to trypsin digestion. From a result of the analysis of its amino acid composition, it was shown that the *Solenocera melantho* DNase is highly bridged intramolecularly through 18 disulfide bonds by 36 Cys residues.

ii) *Penaeus japonicus* (Kuruma Shrimp) DNase

A nuclease having similar molecular weight has also been purified from the hepatopancreas of *Penaeus japonicus* of the family Penaeidae (*Biochim Biophys Acta*, 1209, 209-214 (1994)), and its cDNA sequence has been revealed (*Biochem J*, 346 Pt 3, 799-804(2000)). In addition to its DNase activity, the *Penaeus japonicus* nuclease showed a low level of RNase activity. Based on the homology of amino acid sequences, it was shown that the *Penaeus japonicus* nuclease belongs to the family of DNA/RNA nonspecific endonuclease (DRNSN) typified by the *Serratia marcescens* nuclease, rather than the bovine DNA degrading enzyme I-like protein (bovine DNase-I-like protein). Amino acid sequence of the *Penaeus japonicus* nuclease has 402 amino acid residues and consists of a mature enzyme of 381 residues and a presumed signal peptide of 21 residues. The *Penaeus japonicus* nuclease has 11 Cys residues, and 10 Cys residues among them formed 5 intramolecular disulfide bonds, and the remaining one Cys residue was linked to a thiol compound having an estimated molecular weight of from 500 to 700 Da. Wang et al. have succeeded in expressing a cloned nuclease gene in *Escherichia coli*, but the expressed protein did not show the nuclease activity (*Biochem J*, 346 Pt 3, 799-804(2000)).

iii) *Paralithodes camtschaticus* (King Crab) DSN

A nuclease having similar molecular weight has also been purified from the hepatopancreas of *Paralithodes camtschaticus* of the family Lithodidae, Anomala (Биохимия.58,681-691(1993) (*Biokhimia*, 58,681-691(1993)), and its cDNA sequence has been revealed (*Genome Res*,12,1935-1942 (2002)). Amino acid sequence of the *Paralithodes camtschaticus* nuclease has 407 amino acid residues and consists of a mature enzyme of 380 residues and a presumed signal peptide of 27 residues, and has a homology of 64% with the *Penaeus japonicus* nuclease.

Although the nuclease sequence of *Paralithodes camtschaticus* had also an NUC domain which is common to the DRNSN, as a result of characterization of the purified enzyme, to our surprise, the *Paralithodes camtschaticus* nuclease showed strong digestion selectivity for a double-stranded DNA substrate and hardly showed its activity for a single-stranded DNA. Also, the *Paralithodes camtschaticus* nuclease hardly showed digestion activity for an RNA substrate, and in the case of a DNA-RNA hybrid double strand, efficiently digested its DNA molecule alone. In addition, it hardly showed digestion activity for a short double-stranded DNA containing a mismatch. Thus, characteristic substrate specificity of the *Paralithodes camtschaticus* nuclease was revealed, and this enzyme was called "duplex-specific nuclease" (DSN) (*Genome Res*, 12, 1935-1942(2002), *BMC Biochem*, 9, 14(2008)).

Although Shagin et al. have cloned a cDNA of *Paralithodes camtschaticus* DSN and expressed its mature *Paralithodes camtschaticus* DSN, prepared by removing a presumed signal peptide, in *Escherichia coli* as an N-terminal His-tag fusion protein, the recombinant protein did not have the enzyme activity (*Genome Res*, 12, 1935-1942(2002)). Anisimova et al. have succeeded in purifying a soluble recombinant *Paralithodes camtschaticus* DSN having enzyme activity from an inclusion body in which the recombinant DSN molecule was aggregated in *Escherichia coli*, through a series of procedures including denaturation, refolding and activation (*Biochemistry (Mosc)*,71,513-519(2006)). Additionally, the inventors of the present invention have previously isolated a *Paralithodes camtschaticus* DSN gene, and carried out expression of a recombinant *Paralithodes camtschaticus* DSN from said DSN gene having a signal peptide sequence, using a baculovirus-insect cell expression system. As a result, the inventors of the present invention have succeeded in expressing and purifying a soluble recombinant *Paralithodes camtschaticus* DSN which does not require refolding, and the thus obtained recombinant DSN showed a duplex-specific nuclease activity which was similar to that of the natural origin DSN (Expression of duplex-specific nuclease derived from *Paralithodes camtschaticus* by insect cells-baculovirus system. Eleventh Annual Meeting of Japanese Society for Marine Biotechnology P4-1(May 24 to May 25 in 2008)).

iv) *Pandalus borealis* (a Red Shrimp) DSN

It has been shown that a nuclease purified from the digestive gland of *Pandalus borealis* of the family Pondalidae, Caridea also has digestion selectivity for a double-stranded DNA substrate and hardly degrades single-stranded DNA (WO99/07887). In contrast to the *Paralithodes camtschaticus* DSN, this *Pandalus borealis* DSN is a heat-labile enzyme which has an optimum activity temperature of 25° C. and is inactivated by a heating at 70° C. for 30 minutes or at 94° C. for 2 minutes. As an application of the *Pandalus borealis* DSN making use of this heat-labile nature, a method for removing carry over contamination of PCR products has been disclosed (WO99/07887), although amino acid sequence and cDNA sequence of the *Pandalus borealis* DSN are not disclosed.

v) Other DSN Homologues

DSN homologues having homology with the amino acid sequence of *Paralithodes camtschaticus* DSN have been found in some species of Decapoda. Molthathong et al. have isolated a cDNA encoding for a DSN homologue from the hepatopancreas of *Penaeus monodon* (black tiger shrimp) of the family Penaeidae. Its estimated amino acid sequence was possessed of 89% of homology with the sequence of *Penaeus japonicus* (*Fish Shellfish Immunol*, 22, 617-627(2007)). As other DSN homologous sequences, a mRNA sequence derived from *Amphiuca crassioes* (a red fiddler crab) of the family Ocypedidae [GenBank DQ862540] and a mRNA sequence derived from a Palaemonidae sp. (a species of the family Palaemonidae) [GenBank DQ862538] are found in the GenBank sequence data base. Classification of the *Paralithodes camtschaticus* DSN and other DSN homologues as novel nuclease family based on the evolutionary genealogical tree analysis has been proposed (*Gene*, 418, 41-8(2008). Since there are no reports on these DSN homologue sequences regarding the isolation and enzyme activity of each protein, it is not yet confirmed whether or not these are translated actually as proteins having nuclease activities, whether or not the translation products have duplex-specific nucleic acid digestion activities such as of the *Paralithodes camtschaticus* DSN, and whether or not these have heat resistance.

In summary, those in which the duplex-specific nuclease activity was actually shown among the Decapoda-derived DSN, DSN-like nucleases and DSN homologues are only two species of the DSN of *Paralithodes camtschaticus* belonging to Anomura (Anomara) and DSN of *Pandalus borealis* belonging to Caridea. While the former has a heat resistance having an optimum activity temperature of around 60° C., the latter is a heat-labile enzyme having an optimum activity temperature of 25° C. A DSN which shows a duplex-specific nuclease activity and a DSN having heat resistance, which were derived from an organism belonging to Brachyura, for example derived from an organism belonging to the family Majidae, such as a genus *Chionoecetes*-derived, for example a *Chionoecetes opilio* (snow crab)-derived counterparts, have not so far been disclosed.

Although Other than the case of Decapoda, an enzyme which shows a duplex-specific nuclease activity has been found for example in an insect *Culex quinquefasciatus* (*J Exp Biol*, 209 (Pt 14), 2651-9(2006)), heat resistance of said enzyme was not confirmed and its expression is limited to the salivary gland of female adults. Therefore, it seems difficult to industrially apply this enzyme by isolating it from the nature.

Namely, the nuclease derived from the hepatopancreas of *Paralithodes camtschaticus* was the only one heat-resistant DSN which is industrially applicable. Since the *Paralithodes camtschaticus* DSN has a characteristic selectivity for the digestion of nucleic acid molecules and it has heat resistance and shows its activity at high temperature, its various applications in the field of molecular biology have been shown. For example, SNP analysis (*Genome Res*, 12,1935-1942(2002), WO03/048378), normalization of cDNA library (*Nucleic Acids Res*, 32, e37(2004)), subtraction (*Anal Biochem*, 372, 148-155(2008)) and analysis of telomere single strand overhand length (*Nucleic Acids Res*, 36, e14(2008)) and the like have been disclosed. However, the commercially available *Paralithodes camtschaticus* DSN enzyme reagents are purified products from the nature and therefore are considerably expensive. Although the recombinant *Paralithodes camtschaticus* DSN expressed in *Escherichia coli* is accumulated as an inactive inclusion body in the cell and it can be isolated as an active type enzyme after passing through solubilization, refolding and the like processes (*Biochemistry (Mosc)*,71,513-519(2006)), the procedure requires multiple steps and therefore is complex.

Under such a background, a novel thermostable DSN enzyme has been in demand. Also, a novel thermostable DSN enzyme which can be easily produced making use of recombinant protein expression techniques has been in demand. Additionally, a novel thermostable DSN enzyme, derived from an organism belonging to Brachyura, for example derived from an organism of the family Majidae, for example derived from the genus *Chionoecetes*, has been in demand.

SUMMARY OF THE INVENTION

A main problem to be solved by the inventors of the present invention is to obtain novel thermostable duplex-specific nuclease (DSN) gene and enzyme. Also, another problem is to obtain a novel thermostable DSN which can be easily produced making use of recombinant protein expression techniques and to provide a production method thereof. Still another problem is to obtain a novel thermostable DSN, derived from an organism belonging to Brachyura, more illustratively derived from an organism of the family Majidae, further illustratively derived from the genus *Chionoecetes*. Additionally, a further problem is to provide a method for digesting nucleic acid using a novel thermostable DSN and a method for detecting RNA using said DSN, and a reagent kit to be used in the aforementioned methods.

This and other objects of the present invention have been achieved by the followings:

[1] A protein of the following (a) or (b):
(a) a protein consisting of the amino acid sequence represented by SEQ ID NO:2;
(b) a protein consisting of an amino acid sequence, wherein one or two or more amino acids in the amino acid sequence represented by SEQ ID NO:2 are added, deleted, inserted or substituted, and also having a duplex-specific nuclease activity;

[2] The protein according to the above [1], which has a heat resistance of the following (a) or (b):
(a) a heat resistance which can show the duplex-specific nuclease activity within a range of at least from about 20° C. to 63° C.;
(b) a heat resistance which can maintain, after heating at 60° C. for 30 minutes, at least about 80% of the duplex-specific nuclease activity of activity before the heating;

[3] The protein according to the above [2], which has such a heat resistance that it can show the duplex-specific nuclease activity within a range of from about 55° C. to 63° C.;

[4] The protein according to any one of the above [1] to [3], wherein its molecular weight by SDS polyacrylamide gel electrophoresis is from 42,000 to 46,000, and its isoelectric point is 4.4;

[5] The protein according to any one of the above [1] to [4], which shows the duplex-specific nuclease activity in the presence of $Mg^{2+}$ ion or $Mn^{2+}$ ion and is insensitive to $Ca^{2+}$ ion;

[6] The protein according to any one of the above [1] to [5], which is derived from an organism belonging to Brachyura;

[7] The protein according to any one of the above [1] to [6], which is derived from the hepatopancreas of the genus *Chionoecetes;*

[8] The protein according to any one of the above [1] to [7], which is derived from *Chionoecetes opilio;*

[9] A gene which encodes the protein described in any one of the above [1] to [8];

[10] A gene consisting of a DNA of the following (a) or (b):
(a) a DNA consisting of the nucleotide sequence represented by SEQ ID NO:1;
(b) a DNA which hybridizes with a DNA consisting of the nucleotide sequence represented by SEQ ID NO:1 or a DNA consisting of a nucleotide sequence complementary to said DNA under a stringent condition, and also encodes a protein having a duplex-specific nuclease activity;

[11] A recombinant vector which comprises the gene described in the above [9] or [10];

[12] A transformed cell or transduced cell, which comprises the recombinant vector described in the above [11];

[13] A method for producing a protein having a duplex-specific nuclease activity, which comprises culturing the transformed cell or transduced cell described in the above [12] using a medium and collecting the protein having a duplex-specific nuclease activity from the cultured mixture;

[14] The method according to the above [13], wherein the protein having a duplex-specific nuclease activity is expressed in an insect cell;

[15] A method for digesting a nucleic acid, which comprises using the protein described in any one of the above [1] to [8] or a protein having a duplex-specific nuclease activity produced by the method described in the above [13] or [14];

[16] The method according to the above [15], wherein a double-stranded DNA is preferentially digested, rather than a single-stranded DNA, in a system in which the single-stranded DNA and double-stranded DNA coexist;

[17] The method according to the above [15], wherein the DNA chain in a DNA-RNA hybrid double chain is preferentially digested;

[18] The method according to any one of the above [15] to [17], which is a method for digesting a duplex-specific nucleic acid, wherein the reaction is carried out under a condition of 50° C. or more;

[19] The method according to the above [18], wherein the reaction is carried out under a condition of 60° C. or more;

[20] A method for detecting an RNA, which comprises the following steps (i) to (iii):
(i) a step for forming a DNA-RNA hybrid chain;
(ii) a step for degrading the DNA in the DNA-RNA hybrid chain formed by the step (i), using the protein described in any one of the above [1] to [5] or a protein having a duplex-specific nuclease activity produced by the method described in the above [13] or [14]; and
(iii) a step for detecting the presence of the RNA, by detecting the degradation of DNA in the step (ii);

[21] The method according to the above [20], which is an RNA detection method for detecting an RNA having a specific nucleotide sequence, wherein a DNA-RNA hybrid chain of the RNA to be detected and a probe DNA having a nucleotide sequence complementary to said RNA is formed in the aforementioned step (i); and

[22] A reagent kit, which comprises at least one of the protein described in any one of the above [1] to [8] or a protein having a duplex-specific nuclease activity produced by the method described in the above [13] or [14].

BRIEF DESCRIPTION OF THE DRAWINGS

FIG. 2 is a multiple alignment figure showing comparison of amino acid sequences of *Chionoecetes* (snow crab) DNS (Zuwai disclosed as SEQ ID NO: 2), *Penaeus japonicus* (kuruma shrimp) DNase (Kuruma disclosed as SEQ ID NO: 23) and *Paralithodes camtschaticus* (king crab) DSN (Taraba disclosed as SEQ ID NO: 24).

FIG. 13 discloses SEQ ID NOS: 21, 25, 21, 25, 26, 27, 25, 28, 27 and 25, respectively, in order of appearance.

DETAILED DESCRIPTION OF THE INVENTION

Figure 1:
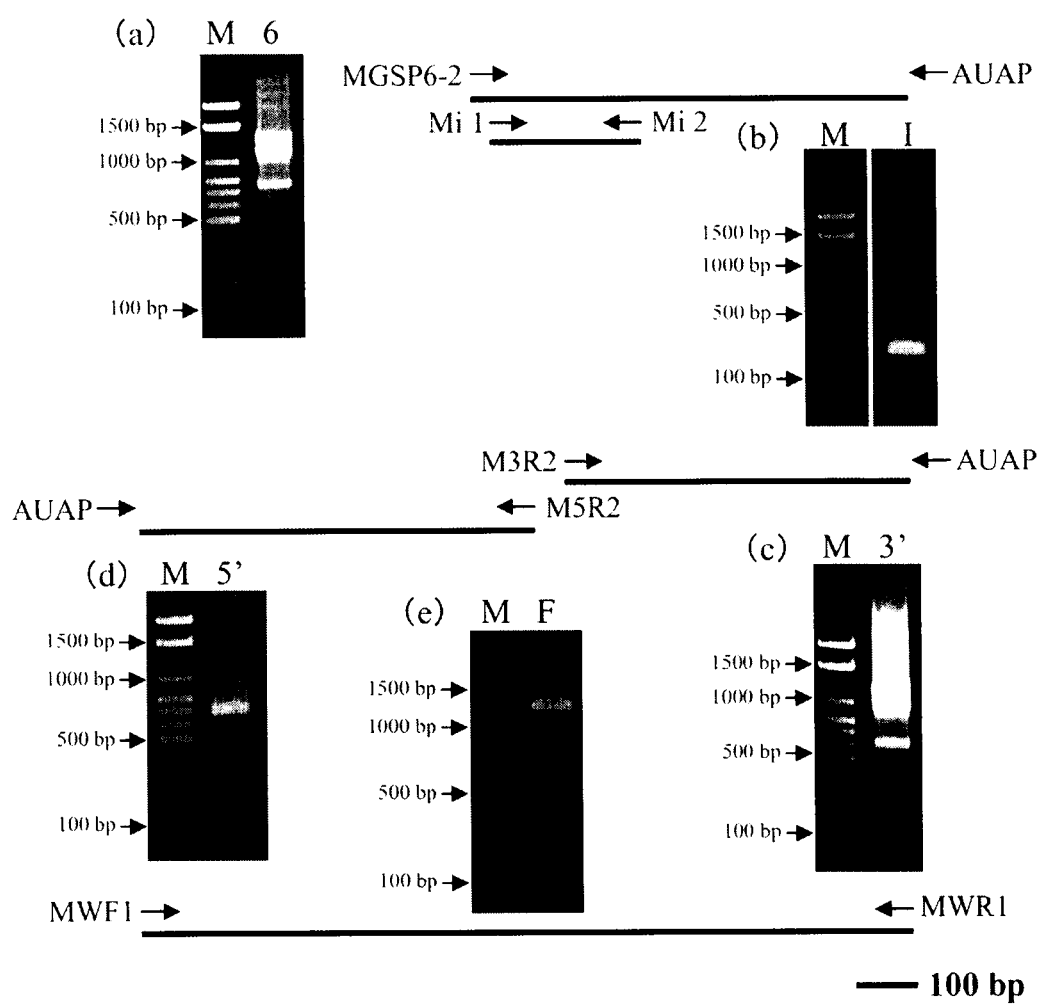
FIG. 1 is a figure showing an outline of the cloning of partial sequence and complete sequence of *Chionoecetes* (snow crab) DSN gene.

With the aim of solving the above-mentioned problems, the inventors of the present invention have conducted intensive studies and found as a result that a mRNA encoding for a DSN-like polypeptide sequence is expressed in the hepatopancreas of a species of the genus *Chionoecetes, Chionoecetes opilio* (snow crab), among the organisms belonging to Brachyura, and have isolated a cDNA from said mRNA in the snow crab hepatopancreas-derived total RNA and thereby revealed that said gene encodes a protein which can actually show the DSN activity. By further finding that said protein has a heat resistance and also finding a method for easily producing said protein making use of a recombinant protein expression technique, an invention which can solve the above-mentioned problems has been accomplished.

The following describes the present invention in detail.

According to the present invention, the DSN (duplex-specific nuclease) means an enzyme which has the ability to show a DSN activity (duplex-specific nuclease activity), and said DSN activity means an activity to preferentially digest or degrade deoxyribonucleic acid existing in a double-stranded nucleic acid. A DNA-DNA double strand, a DNA-RNA double strand and a double strand moiety in a nucleic acid molecule having a partial single strand structure and a partial double strand structure are included in said double-stranded nucleic acid. Said partial single strand structure includes, for example, mismatch of bases, bulge structure, loop structure, flap structure and pseudo-Y structure and the like.

An example of the DSN activity is an activity to degrade a double-stranded DNA preferentially, rather than a single-stranded DNA, in a system in which the single-stranded DNA and double-stranded DNA coexist. Also, an example of another DSN activity is an activity to preferentially degrade a DNA chain in a DNA-RNA hybrid double strand. Additionally, an example of still another DSN activity is an activity to preferentially degrade a double-stranded nucleic acid moiety which forms perfect base pairs, in a system in which the double-stranded nucleic acid that forms perfect base pairs and a double-stranded nucleic acid containing a mismatch are present.

The DSN activity can be measured for example by the Kunitz method (*Gen. Physiol.*, 33, 349-362, 1950). Additionally, the DSN activity can also be detected for example by allowing a purified enzyme to undergo the reaction at 37° C. for 30 minutes using a nucleic acid as the substrate, carrying out an agarose gel electrophoresis and comparing the presence or absence and light and shade of the band of the substrate.

The thermostable DSN of the present invention has such a heat resistance that it can show a high activity at least within a range of from about 20° C. to about 63° C., preferably can show particularly high activity within a range of from about 55° C. to about 63° C., and particularly preferably can show optimum activity at about 60° C. In this connection, said activity means the DSN activity. For example, when the activity of a purified enzyme is measured by the activity measuring method shown by the examples of this application using a bovine thymus-derived DNA, it is desirable that it shows a DNA degradation activity of from 800 U/ml to 73,000 U/ml within a range of from about 20° C. to about 63° C., preferably shows a DNA degradation activity of from 46,000 U/ml to 73,000 U/ml within a range of from about 55° C. to about 63° C., and particularly preferably shows a DNA degradation activity of from 63,000 U/ml to 73,000 U/ml at about 60° C. Additionally, another aspect of the heat resistance possessed by the enzyme of the present invention is such a heat resistance that it can keep at least about 80%, preferably about 90%, of the activity of before the heating.

Although the thermostable DSN of the present invention can show particularly high activity within a range of from about 55° C. to about 63° C. as described in the above, it can show a sufficient activity even at a low temperature (e.g., 25° C.) as its illustrative example were shown the examples of this specification. Namely, the thermostable DSN of the present invention can be used within a broad temperature range of from a low temperature to a high temperature (about 63° C.). Additionally, even in the case of a temperature of higher than 63° C., when periodical inactivation of the enzyme is not a problem, it can also be used at a high temperature of within such a range that the activity of this enzyme does not completely disappear (e.g., a temperature of not exceeding 80° C., such as 70° C.).

The thermostable DSN of the present invention is a DSN derived from an organism belonging to Brachyura, more illustratively derived from an organism belonging to Majidae, further illustratively derived from the genus *Chionoecetes*.

Examples of the DSN derived from the genus *Chionoecetes* include the DSN derived from *Chionoecetes angulatus, Chionoecetes bairdi, Chionoecetes japonicus, Chionoecetes opilio* and *Chionoecetes tanneri*, preferably, include the DSN derived from *Chionoecetes japonicus* and *Chionoecetes opilio*, and more preferably include the DSN derived from *Chionoecetes opilio*. In this connection, in addition to its Japanese standard Japanese name snow crab, the *Chionoecetes opilio* is also called "matsuba crab" or "echizen crab" and by other regional names.

One of preferable embodiments of the thermostable DSN of the present invention is a DSN having an amino acid sequence of the *Chionoecetes opilio*-derived DSN or an amino acid sequence in which one or two or more amino acids of said amino acid sequence are added, deleted, inserted or substituted. In this case, the amino acid sequence of the *Chionoecetes opilio*-derived DSN is for example the amino acid sequence represented by SEQ ID NO:2. It is preferable that molecular weight of the thermostable DSN of the present invention is from 42,000 to 46,000 when measured by an SDS polyacrylamide gel electrophoresis. Also, it is preferable that isoelectric point of the thermostable DSN of the present invention is 4.4.

Additionally, it is preferable that the thermostable DSN of the present invention shows suitable DSN activity in the presence of $Mn^{2+}$ ion or $Mg^{2+}$ ion but is insensitive to $Ca^{2+}$ ion. For example, when the activity of a purified enzyme is measured by the activity measuring method shown by the examples of this application using a bovine thymus-derived DNA, it is preferable that it shows a relative activity of from 75% to 100% in the case of using $Mn^{2+}$ ion within a range of from 1 mM to 4 mM, or a relative activity of from 70% to 100% in the case of using $Mg^{2+}$ ion within a range of from 7 mM to 30 mM. Additionally, when $Ca^{2+}$ ion is used within a range of from 0 to 100 mM, it is preferable that it hardly shows the activity similar to the case of not adding metal ions.

In this case, the amino acid sequence in which one or two or more amino acids are added, deleted, inserted or substituted means an amino acid sequence having an amino acid sequence homology of at least 75%, preferably at least 80%, more preferably at least 85%, further preferably at least 90%, most preferably at least 95%, in comparison with a basis sequence.

A preferable embodiment of the thermostable DSN of the present invention is an enzyme purified from the hepatopancreas of the genus *Chionoecetes*, for example an enzyme purified from the hepatopancreas of *Chionoecetes opilio*. Based on the disclosure of the present invention that *Chionoecetes opilio* is expressing a thermostable DSN in its hepatopancreas, those skilled in the art can isolate and purify the thermostable DSN of the present invention from the hepatopancreas of an organism belonging to the genus *Chionoecetes*, for example, by using general biochemical techniques such as gel filtration chromatography, ion exchange chromatography, affinity chromatography, centrifugation, concentration, dialysis and the like, alone or in an optional combination. Additionally, those skilled in the art can purify it also by the disclosed purification methods of similar hepatopancreas-derived enzymes, such as the purification method of DNase from *Solenocera melantho* hepatopancreas (*Biochim Biophys Acta*, 1036, 95-100(1990)) and the purification methods of DSN from *Paralithodes camtschaticus* hepatopancreas (Биохимия.58,681-691(1993) (*Biokhimia*,58,681-691 (1993), *Genome Res,* 12,1935-1942(2002), *BMC Biochem,* 9, 14(2008)), and applied methods thereof and modified methods thereof.

Although the thermostable DSN of the present invention may be isolated and purified from a natural living body-derived material as described in the foregoing, it may also be prepared as a recombinant protein making use of a gene encoding for the thermostable DSN of the present invention.

The gene encoding for the thermostable DSN of the present invention is prepared by a conventionally known method such as a cloning technique and the like to those skilled in the art, based on the SEQ ID NO:1 or SEQ ID NO:2 of this specification. For example, said gene can be prepared as a cDNA from total RNA derived from the hepatopancreas of *Chionoecetes opilio*. Additionally, said gene is prepared, for example, by the method described in Example 3 of this specification based on the disclosed sequences.

Additionally, the aforementioned DNA having a nucleotide sequence encoding for the amino acid sequence of the thermostable DSN is also included in the gene encoding for the thermostable DSN of the present invention. Also, a DNA which hybridizes with said DNA or a DNA consisting of a sequence complementary to said DNA under a stringent condition and which encodes a protein having the DSN activity is also included in the gene of the present invention. Additionally, a DNA which has a nucleotide sequence in which one or two or more bases in a DNA having a nucleotide sequence encoding for the thermostable DSN described in SEQ ID NO:1 are added, deleted or substituted, and which also has a nucleotide sequence encoding for the thermostable DSN, is also included in the gene of the present invention. In this case, the nucleotide sequence in which one or two or more bases are added, deleted, or substituted means a nucleotide sequence having a nucleotide sequence homology of at least 75%, preferably at least 80%, more preferably at least 85%, further preferably at least 90%, most preferably at least 95%, in comparison with a basis sequence.

In this case, the "stringent condition" means a condition under which a so-called specific hybrid is formed and non-specific hybrids are not formed. Although it is difficult to express this condition numerically and distinctly, for example, it is a condition under which a pair of nucleic acids having high homology, such as a pair of DNA having 70% or more, preferably 80% or more of homology, are hybridized but other nucleic acids having homology of lower than that are not hybridized. For example, the conditions are described in Molecular Cloning—A Laboratory Manual, $2^{nd}$ edition (Sambrook et al., 1989), and the like. Namely, examples of the conditions include a condition for effecting hybridization by incubating a solution containing 6×SSC (composition of 1×SSC: 0.15 M sodium chloride and 0.015 M sodium citrate, pH 7.0), 0.5% SDS, 5×Denhardt and 100 mg/ml of herring sperm DNA at 65° C. for a period of from 8 to 16 hours together with a probe, and the like can be exemplified.

Also, in addition to the method for preparing a thermostable DSN from an organism-derived material, a desired thermostable DSN gene can be directly synthesized by an organic synthesis method, an enzymatic synthesis method or an optionally combined method thereof, based on the confirmed thermostable DSN nucleotide sequence information.

The recombinant DNA of the present invention can be obtained by connecting the gene of the present invention to (inserting into) an appropriate vector. The vector into which the gene of the present invention is inserted is not particularly limited with the proviso that it is replicable in its host, and examples thereof include a plasmid DNA, a phage DNA and the like can be exemplified. Examples of the plasmid DNA include plasmids derived from *Escherichia coli* (e.g., pBR322, pBR325, pUC8, pUC9, pUC118, pUC119, pET (manufactured by Novagen), pGEX (manufactured by Amersham Biosciences), pQE (manufactured by QIAGEN), pMAL (manufactured by New England Biolabs) and the like), plasmids derived from *Bacillus subtilis* (e.g., pUB110, pTP5 and the like), plasmids derived from yeast (e.g., YEp13, YEp24, YCp50 and the like) and the like. Examples of the phage DNA include λ phage and the like. In addition to these, the examples include retrovirus, vaccinia virus and the like animal virus vectors and baculovirus and the like insect virus vectors.

For inserting the gene of the present invention into a vector, for example, a method in which a DNA containing purified gene of the present invention is digested with appropriate restriction enzymes, inserted into restriction enzyme sites or a multi-cloning site of an appropriate vector DNA and thereby connected to the vector, or the like is employed. In addition to a promoter and the gene of the present invention, an enhancer or the like cis element, a splicing signal, a poly (A) addition signal, a selection marker, a ribosome binding sequence (SD sequence) and the like can be connected to the vector as occasion demands. Examples of the selection marker include a dihydrofolate reductase gene, an ampicillin resistance gene, a neomycin resistance gene and the like. In order to facilitate purification and detection of the thermostable DSN of the present invention later, or in order to prevent insolubilization of the expressed thermostable DSN in cells, a sequence which encodes GST tag, histidine tag or the like tag sequence and the like may be added to the gene of the present invention (e.g., Appl. Microbiol. Biotechnol., 60, 523-533, 2003).

The transformed cell and transduced cell of the present invention can be obtained by introducing the recombinant vector of the present invention into a host in such a manner that the gene of interest can be expressed. The host to be used herein is not particularly limited with the proviso that it can express the gene of the present invention. Example thereof include, bacteria belonging to the genus *Escherichia* (*Escherichia coli* or the like), the genus *Pseudomonas* (*Pseudomonas putida* or the like), the genus *Bacillus* (*Bacillus subtilis* or the like), the *Rhizobium* (*Rhizobium meliloti* or the like) and the like, *Saccharomyces cerevisiae*, *Schizosaccharomyces pombe* and the like yeasts, COS cell, CHO cell and the like animal cells and an army worm cell (Sf9, Sf21 or the like) and a silkworm cell (BmN4 or the like) and the like insect cells.

When the transformed cell or transduced cell of the present invention is obtained, enzyme collection means the collection generally carried out by those skilled in the art can be used for collecting the thermostable DSN of the present invention from its cultured product. When the thermostable DSN of the present invention is produced in a microbial body or cell, said enzyme can be extracted by disintegrating the microbial body or cell. For example, said enzyme can be extracted from the microbial body or cell by a method in which a microbial body or cell is subjected to an ultrasonic disintegration treatment, grinding treatment or the like in the usual way, a method in which said enzyme is extracted using lysozyme or the like lytic enzyme, or a method in which said enzyme is discharged into outside moiety of the microbial body or cell by shaking it or leaving it in the presence of toluene or the like to cause its autolysis.

When a purified enzyme preparation is obtained from the thus obtained preparation containing the thermostable DSN of the present invention, by further purifying the thermostable DSN of the present invention, the thermostable DSN of the present invention can be isolated and purified from the aforementioned enzyme solution by carrying out general biochemical methods used by those skilled in the art for the isolation and purification of protein, such as ammonium sulfate precipitation, gel chromatography, ion exchange chromatography, affinity chromatography and the like, alone or in an optional combination.

When the thermostable DSN of the present invention is expressed by adding GST tag, histidine tag or the like tag sequence and the like thereto, such an addition sequence may be removed in the middle of purification or after purification of said enzyme by an appropriate enzyme treatment generally carried out by those skilled in the art, or the like, or may be used as such when activity of the thermostable DSN of the present invention is not spoiled by the addition sequence.

It is known that the *Solenocera melantho* hepatopancreas-derived DNase and bovine pancreas-derived DNase show resistance to trypsin digestion (*Biochim Biophys Acta*, 1036, 95-100(1990)) and the *Paralithodes camtschaticus* hepatopancreas-derived DSN shows resistance to proteinase digestion (*BMC Biochem*, 9, 14(2008)). On the other hand, the inventors have found that the genus *Chionoecetes opilio*-derived thermostable DSN of the present invention shows resistance to proteinase K digestion. Based on this disclosure, although those skilled in the art can conveniently carry out purification of the enzyme of the present invention by treating under such a condition that the majority of unintended proteins are digested by proteinase K the intended thermostable DSN of the present invention is not degraded. An example of the preferable embodiment of the method for producing the thermostable DSN of the present invention, which includes such a purification procedure, is illustratively described further in detail in the examples of this specification.

As can be understood from the disclosed amino acid sequence, the thermostable DSN of the present invention has cysteine residues to a high degree, so that it is considered based on this that two or more disulfide bridges are formed in the molecule. It is known to those skilled in the art that, generally in the case of a protein which has a high degree intramolecular disulfide net work, there are many cases in which it is difficult to obtain a recombinant protein successfully using *Escherichia coli* or the like prokaryote as the host. When the protein of interest expressed in *Escherichia coli* is obtained as insolubilized inclusion body, the protein of interest which is soluble and has the enzyme activity can be regenerated via steps such as solubilization, refolding and the like of the inclusion body (e.g., *Biochemistry (Mosc)*,71,513-519(2006)).

An example of the preferable embodiment of the method for preparing the thermostable DSN of the present invention as a recombinant protein is a method for expressing the protein of interest in a eukaryotic cell, a preferable example thereof is a method for expressing the protein of interest in an insect cell, and for example, a method which uses a baculovirus-insect cell recombinant protein expression system in which a protein of interest is expressed in a recombinant baculovirus-infected insect cell (e.g., a literature of Shuler, M. L. et al., "Baculovirus Expression Systems and Biopesticides", John Wiley and Sons, New York, 1995 and a literature of O'Reilly, D. R. et al., "Baculovirus Expression Vectors: A Laboratory Manual", Oxford University Press, New Yolk, 1994) can be cited. An example of the preferable embodiment of the method for producing the thermostable DSN of the present invention, which uses a baculovirus-insect cell recombinant protein expression system, is described illustratively and further in detail in the examples of this specification.

By the use of the thermostable DSN of the present invention, a method for digesting a nucleic acid using said enzyme is provided. According to said method, a nucleic acid can be digested duplex-specifically. More in detail, according to said method, a double-stranded DNA can be preferentially degraded rather than a single-stranded DNA in a system in which the single-stranded DNA and double-stranded DNA coexist. Also, according to said method, the DNA chain in a DNA-RNA hybrid double chain can be degraded preferentially. When a nucleic acid is duplex-specifically digested using the thermostable DSN of the present invention, it is preferable to carry out the reaction under a condition of 40° C. or more; it is more preferable under a condition of 50° C. or more; and it is further preferable under a condition of 60° C. or more. Additionally, it is preferable to carry out the reaction under a condition of 70° C. or less and it is more preferable to carry out the reaction under a condition of 65° C. or less.

The reaction liquid composition and reaction conditions in the nucleic acid digestion method which uses the thermostable DSN of the present invention can be optionally selected by those skilled in the art in response to the purpose. For example, the reaction liquid composition and reaction conditions described in the examples of this specification and modifications thereof can be used, although not limited thereto. As described in the foregoing, although the thermostable DSN of the present invention can show particularly high activity within the range of from about 55° C. to about 63° C., the applicable reaction temperature is not limited to this range.

The thermostable DSN of the present invention can show sufficient activity even at a low temperature (e.g., 25° C. (cf., Examples)). Additionally, in the case of a using purpose which is unrelated to the problem of inactivation of the enzyme accompanied by the lapse of time, it can also be used within such a high temperature range that the activity of this enzyme does not completely disappear (e.g., a temperature which does not exceed 80° C., 70° C. for example). Namely, since the thermostable DSN of the present invention can show its activity within a broad temperature range of from a low temperature to a high temperature, those skilled in the art can use it under various temperature conditions in response to the purpose. For example, the nucleic acid digestion method of the present invention can be carried out by using the thermostable DSN of the present invention under a constant temperature condition, under a condition which accompanies a change in temperature within a certain range, under a predetermined or programmed temperature cycling condition and the like.

By the use of the thermostable DSN of the present invention, an RNA detection method which comprises the following steps (i) to (iii) is provided;
(i) a step for forming a DNA-RNA hybrid chain,
(ii) a step for degrading DNA in the DNA-RNA hybrid chain formed by the step (i), with the thermostable DSN of the present invention, and
(iii) a step for detecting the presence of RNA, by detecting the degradation of DNA in the step (ii).

By the step (i), an RNA having specific nucleotide sequence can be detected by effecting formation of a DNA-RNA hybrid chain of the RNA to be detected and a probe DNA having a nucleotide sequence complementary to said RNA.

The following describes respective steps.
(i) A step for forming a DNA-RNA hybrid chain This step is a step for effecting formation of a hybrid chain of an RNA and a DNA having a nucleotide chain complementary to said RNA. The term "hybrid" as used herein means a result of the complementary binding of the RNA and DNA. Examples of the RNA include in addition to the case of an entirely natural type RNA, a nucleic acid containing an RNA in its part, an RNA containing an unnatural type nucleotide, and the like. Additionally, according to the method of the present invention, an RNA fragment can also be detected.

The RNA may be present in a solution or in a solid state. Additionally, it may be in a state of being immobilized, through complementary binding, on a solid phase carrier which is called a DNA chip or DNA array. In the case of its solution, water or a buffer solution is preferable as the solvent, and in addition to water, it is preferable to use a solvent which can be mixed with water by optionally mixing therewith. Examples of the solvent which is used by mixing with water include methanol, ethanol, propanol, isopropanol, glycerol, ethylene glycol, dimethylformamide, dimethyl sulfoxide, dimethylacetamide, tetrahydrofuran, acetonitrile, sulfolane and the like. In the case of the solid state, the RNA to be detected may be under a mixed condition with other substance or may be a mixture of two or more RNA species.

When RNA is immobilized on the solid phase carrier, examples of said solid phase carrier include ceramics or new ceramics such as glass, cement, chinaware or the like, polymers such as polyethylene terephthalate, cellulose acetate, polycarbonate of bisphenol A, polystyrene, polymethyl methacrylate and the like and porous materials such as silicon, activated carbon, porous glass, porous ceramics, porous silicon, porous activated carbon, woven fabric, non-woven fabric, filter paper, single fiber, membrane filter and the like. Also, the solid phase carrier may be a beads-like product or a gelled product such as acrylamide gel. Furthermore, the RNA may be simply adhered closely onto the solid phase carrier physically or may be in a form of being partially permeated into the solid phase carrier from the surface of the solid phase carrier. Additionally, the RNA may be in a form of being completely permeated into the solid phase carrier or may be chemically linked to the solid phase carrier by covalent bonding.

Examples of the DNA to be used for forming a DNA-RNA hybrid chain include a chemically synthesized DNA, a DNA enzymatically synthesized by a DNA polymerase and a reverse transcriptase and a DNA extracted or cloned from a organism-derived sample. Also, in the case of detecting nucleotide sequence of a specific RNA, it is preferable that the DNA to be used for forming a DNA-RNA hybrid chain is a probe DNA having a nucleotide sequence complementary to the nucleotide sequence of said RNA. Also, it is preferable that said probe DNA is a substance which holds a marker. Examples of the marker include fluorescence dye such as a quencher (e.g., Eclipse (registered trademark) Dark Quencher, TAMRA (registered trademark), MGB or the like), a reporter pigment (e.g., FAM, ROX, TET, HEX or the like) or the like, biotin and a radioisotope. Additionally, examples of other markers include a substance which cannot be detected directly but becomes indirectly detectable through its reaction with a substance that specifically binds with a marker (e.g., avidin), such as a hapten, an antibody and the like. It is preferable that said DNA contains 15 to 300 nucleotides, preferably 15 to 60 nucleotides.

(ii) A step for degrading DNA in the DNA-RNA hybrid chain formed by the step (i), with the thermostable DSN of the present invention This step is a step for degrading DNA in the DNA-RNA hybrid chain consisting of a single RNA chain and a single DNA chain, formed by the step (i), making use of the thermostable DSN of the present invention for specifically digesting double-strand nucleic acid. It is preferable that the reaction of the step (ii) is carried out under a condition of 25° C. or more and it is more preferable that the reaction of the step (ii) is carried out under a condition of 35° C. or more. Also, it is preferable that the reaction is carried out under a condition of 90° C. or less and it is more preferable that the reaction is carried out under a condition of 80° C. or less.

(iii) A step for detecting the presence of RNA, by detecting the degradation of DNA in the step (ii)

This step is a step for detecting the presence of RNA, by detecting the degradation of DNA in the step (ii). The degradation of DNA can be detected, for example, by the following method. A DNA-RNA hybrid chain is formed by the step (i) using a probe DNA prepared by labeling the 5' end of the DNA with a reporter fluorescence dye, and the 3' end with a quencher fluorescence dye. Thereafter, by degrading the DNA in the DNA-RNA hybrid chain using the thermostable DSN of the present invention, the reporter fluorescence dye and quencher fluorescence dye linked to the probe DNA are separated from each other to render possible detection of the reporter fluorescence dye. Namely, the reporter fluorescence dye is detected when RNA is present in the sample to be tested. Additionally, it can also be detected, for example, by various nucleic acid analyzing techniques known to those skilled in the art, such as horizontal gel electrophoresis, capillary gel electrophoresis, mass spectrometry and the like. For example, it is possible also to detect degradation of DNA by comparing electrophoresis patterns in the case of adding and not adding the DSN enzyme of the present invention.

A reagent kit which comprises the thermostable DSN of the present invention is also included in the scope of the present invention. This reagent kit can contain substances which are necessary for carrying out the measurement such as a marker, a buffer solution, a salt and the like. In addition, it may contain substances such as a stabilizer and/or an antiseptic and the like. It is possible to use said reagent kit in the duplex-specific nucleic acid digestion method and RNA detection method of the present invention.

By the present invention, a novel DSN which has the DSN activity and has such a heat resistance that it can show a high activity within a range of at least from about 20° C. to 63° C., preferably can show particularly high activity within a range of from about 55° C. to 63° C., particularly preferably can show optimum activity at about 60° C., or has such a heat resistance that, after heating at 60° C. for 30 minutes, it can keep at least about 80%, preferably about 90%, of the activity of before the heating (to be referred also to as DSN of the present invention hereinafter), a gene encoding for said thermostable DSN, a recombinant DNA containing said gene, a transformed cell or transduced cell containing said recombinant DNA, and a method for producing said thermostable DSN are provided. Additionally, a method for digesting nucleic acid using said thermostable DSN and a method for detecting RNA using said DSN and a reagent kit to be used in the aforementioned methods are provided by the present invention. The thermostable DSN of the present invention can be applied to various inspection techniques, diagnostic techniques and genetic engineering techniques, which include analysis, detection, degradation, synthesis, modification and the like of nucleic acid molecules.

The following describes the present invention further in detail with reference to examples. In this connection, the present invention is not limited to the following examples.

EXAMPLE 1

Preparation of *Chionoecetes opilio* Hepatopancreas-derived cDNA

We have found that DSN is expressed in the hepatopancreas of *Chionoecetes opilio* and, in order to isolate and identify its gene, a hepatopancreas-derived 1st strand cDNA was firstly prepared by the following methods.

(1) Collection of Hepatopancreas from *Chionoecetes opilio*

Fresh *Chionoecetes opilio* landed at Ajiro Port, Tottori, was purchased and dissected to collect the hepatopancreas. About 100 mg portion of the thus collected hepatopancreas was immediately soaked in 1.2 ml of RNAlater (manufactured by QIAGEN) and stored at 4° C. for 16 hours. The thus soaked hepatopancreas was took out using a pair of tweezers, put into a new Eppendorf tube and stored at −80° C. until its use.

(2) Extraction of Total RNA

Total RNA was extracted from the *Chionoecetes opilio* hepatopancreas stored at −80° C. using RNeasy Mini Kit (manufactured by QIAGEN). Procedure of the purification operation was carried out in accordance with the technical specification attached to said purification kit. A 60 μg portion of total RNA was obtained from 30 mg of the hepatopancreas.

(3) Preparation of 1st Strand cDNA

A 1st strand cDNA was synthesized by the reverse transcription reaction shown below. The reaction was carried out using the reagents attached to 3' RACE System for Rapid Amplification of cDNA Ends (manufactured by Invitrogen). As the template, 1 μg (0.5 μl) portion of the total RNA extracted from *Chionoecetes opilio* hepatopancreas was used. After mixing 0.5 μl of the total RNA, 1 μl of a primer AP (SEQ ID NO:16) (10 μM) and 10.5 μl of RNase Free H$_2$O, 10 minutes of heat treatment was carried out at 70° C., followed by quick cooling on ice. As a reaction buffer, 2 μl of a 10 times concentration of a buffer (10×PCR buffer) was added to the mixed liquid after heat treatment (12 μl). Each of dNTP was added thereto to a final concentration of 0.5 mM, and MgCl$_2$ was added to a final concentration of 2.5 mM, and DTT was added to 10 mM, respectively, and the mixture was incubated at 42° C. for 2 minutes. As the transcriptase, 200 U of SuperScript™ II Reverse Transcriptase was added thereto to prepare a reaction liquid (20 μl in total volume). The reaction liquid was incubated at 42° C. for 50 minutes and then incubated at 70° C. for 15 minutes to complete the transcription reaction. The reaction liquid was cooled on ice, and 2.0 U of RNase H was added thereto and incubated at 37° C. for 20 minutes. This solution was used as the 1st strand cDNA solution. As the thermal cycler, Gene Amp PCR System 9600 (manufactured by Perkin Elmer) was used.

EXAMPLE 2

Determination of Nucleotide Sequence of *Chionoecetes opilio* DSN Gene

Using a *Chionoecetes opilio* hepatopancreas-derived 1st strand cDNA prepared by the method of Example 1 as the template, an internal sequence of the DSN gene was firstly obtained, and then a 3' region sequence was determined based on the thus obtained internal sequence. Then a 5' sequence region was determined, thus finally resulting in the determination of nucleotide sequence of complete cDNA of the *Chionoecetes opilio* DSN gene (SEQ ID NO:20). FIG. 1 is an outline of the cloning of a partial sequence and complete sequence of the *Chionoecetes opilio* DSN gene, showing schematic view of the positions of the used primers and agarose gel electrophoresis images of the respective PCR amplification products (lane M; DNA size marker, lane 6; PCR amplification product by primers GSP 6-2 and AUAP, lane I; PCR amplification product by primers Mi 1 and Mi 2, lane 3'; PCR amplification product by primers M3R2 and AUAP, lane 5'; PCR amplification product by primers M5R2 and AUAP, lane F; PCR amplification product by primers MWF 1 and MWR 1).

(1) Preparation of Internal Sequence of *Chionoecetes opilio* DSN Gene

By referring to the regions well preserved among nuclease genes derived from various crustaceans, primers MGSP 6 (SEQ ID NO:3), MGSP 6-2 (SEQ ID NO:4), Mi 1 (SEQ ID NO:5) and Mi 2 (SEQ ID NO:6) were prepared.

An internal sequence of the *Chionoecetes opilio* DSN gene was amplified by the following PCR. As the template, 2 μl of the 1st strand cDNA was used and added to a reaction liquid (50 μl in total volume). As the DNA polymerase, 2.5 U of TaKaRa Taq (manufactured by TAKARA BIO) was added to the reaction liquid. As the reaction buffer, 5 μl of 10 times concentration of a buffer liquid (10×PCR buffer) was added thereto. As the primers, MGSP 6 (SEQ ID NO:3) and AUAP (SEQ ID NO:14) were respectively added to the reaction liquid to be a final concentration of 0.2 μM. Each of dNTP was added to the reaction liquid to be a final concentration of 0.2 mM, and MgCl$_2$ was added to be a final concentration of 1.5 mM, respectively. As the thermal cycler, Gene Amp PCR System 9600 (manufactured by Perkin Elmer) was used. An amplification product (A) was obtained by carrying out a heat treatment of 94° C. for 2 minutes once, and subsequently repeating 35 times of a temperature cycle consisting of 94° C. for 60 seconds, 45° C. for 30 seconds and 72° C. for 3 minutes.

Next, the amplification product (A) was diluted 100 times with sterile ultrapure water, and nested PCR was carried out using this diluted liquid as the template. As the template, 2 μl of the diluted liquid was used and added to a reaction liquid (50 μl in total volume). As the DNA polymerase, 2.5 U of TaKaRa Taq (manufactured by TAKARA BIO) was added to the reaction liquid. As the reaction buffer, 5 μl of 10 times concentration of a buffer liquid (10×PCR buffer) was added thereto. As the primers, MGSP 6-2 (SEQ ID NO:4) and AUAP (SEQ ID NO:14) were respectively added to the reaction liquid to be a final concentration of 0.2 μM. Each of dNTP was added to the reaction liquid to be a final concentration of 0.2 mM, and MgCl$_2$ to be a final concentration of 1.5 mM, respectively. An amplification product (B) was obtained by carrying out a heat treatment of 94° C. for 2 minutes once, and subsequently repeating 35 times of a temperature cycle consisting of 94° C. for 60 seconds, 55° C. for 30 seconds and 72° C. for 3 minutes.

When the amplification product (B) was subjected to an agarose gel electrophoresis and the resulting bands were verified, a specific amplification product was not observed (FIG. 1(*a*) lane 6). Accordingly, PCR was further carried out using the amplification product (B) as the template. The amplification product (B) was diluted 100 times with sterile ultrapure water. As the template, 2 μl portion of the diluted liquid was used and added to a reaction liquid (50 μl in total volume). As the DNA polymerase, 1.0 U of KOD plus (manufactured by TOYOBO) was added to the reaction liquid. As the reaction buffer, 5 μl of 10 times concentration of a buffer liquid (10× KOD-PCR buffer) attached to the KOD plus product was added thereto. As the primers, Mi 1 (SEQ ID NO:5) and Mi 2 (SEQ ID NO:6) were respectively added to the reaction liquid to be a final concentration of 0.3 μM. Each of dNTP was added to the reaction liquid to be a final concentration of 0.2 mM, and MgSO$_4$ to be a final concentration of 1.5 mM, respectively. A heat treatment was carried out once at 94° C. for 2 minutes, and subsequently, a temperature cycle consisting of 98° C. for 10 seconds, 55° C. for 30 seconds and 68° C. for 90 seconds was repeated 35 times. When the amplification product was subjected to an agarose gel electrophoresis, a band was observed at a position of about 250 by (FIG. 1(b) lane 1). This band was recovered from the agarose gel using MinElute Gel Extraction Kit (manufactured by QIAGEN), purified and dissolved in 20 µl of sterile ultrapure water. Procedure of the purification operation was carried out in accordance with the technical specification attached to said purification kit. The thus obtained amplification product was inserted into a pUC18 vector. Nucleotide sequence of the thus obtained recombinant DNA was deciphered by a DNA sequencer. In this manner, an internal sequence of the *Chionoecetes opilio* DSN gene was determined.

(2) Preparation of *Chionoecetes opilio* DSN Gene 3' Region Sequence

Primers M3R1 (SEQ ID NO:7) and M3R2 (SEQ ID NO:8) were prepared based on the thus obtained internal sequence of *Chionoecetes opilio* DSN gene. By the following PCR, 3' region sequence of the *Chionoecetes opilio* DSN gene was amplified. As the template, 2 µl portion of the 1st strand cDNA was used and added to a reaction liquid (50 µl in total volume). As the DNA polymerase, 2.5 U of TaKaRa Taq (manufactured by TAKARA BIO) was added to the reaction liquid. As the reaction buffer, 5 µl of 10 times concentration of a buffer liquid (10×PCR buffer) was added thereto. As the primers, M3R1 (SEQ ID NO:7) and AUAP (SEQ ID NO:14) were respectively added to the reaction liquid to be a final concentration of 0.2 µM. Each of dNTP was added to the reaction liquid to be a final concentration of 0.2 mM, and MgCl$_2$ to was added to be a final concentration of 1.5 mM, respectively. As a thermal cycler, Gene Amp PCR System 9600 (manufactured by Perkin Elmer) was used. An amplification product (C) was obtained by carrying out a heat treatment of 94° C. for 2 minutes once, and subsequently repeating 35 times of a temperature cycle consisting of 94° C. for 60 seconds, 55° C. for 30 seconds and 72° C. for 3 minutes.

Next, the amplification product (C) was diluted 100 times with sterile ultrapure water, and nested PCR was carried out using this diluted liquid as the template. As the template, 2 µl portion of the diluted liquid was used and added to a reaction liquid (50 µl in total volume). As the DNA polymerase, 2.5 U of TaKaRa Taq (manufactured by TAKARA BIO) was added to the reaction liquid. As the reaction buffer, 5 µl of 10 times concentration of a buffer liquid (10×PCR buffer) was added thereto. As the primers, M3R2 (SEQ ID NO:8) and AUAP (SEQ ID NO:14) were respectively added to the reaction liquid to a final concentration of 0.2 µM. Each of dNTP was added to the reaction liquid to be a final concentration of 0.2 mM, and MgCl$_2$ was added to be a final concentration of 1.5 mM, respectively. Heating was carried out at 94° C. for 2 minutes once, and subsequently, a temperature cycle consisting of 94° C. for 60 seconds, 55° C. for 30 seconds and 72° C. for 3 minutes was repeated 35 times. About 600 by of a PCR amplification product (FIG. 1(c) lane 3') was recovered from the agarose gel using MinElute Gel Extraction Kit (manufactured by QIAGEN), purified and dissolved in 10 µl of sterile ultrapure water. Procedure of the purification operation was carried out in accordance with the technical specification attached to said purification kit.

Using Mighty TA-cloning Kit (manufactured by TAKARA BIO), the thus obtained product was inserted into a pMD20-T vector attached to said kit. Procedure of this operation was carried out in accordance with the technical specification attached to said kit. Nucleotide sequence of the thus obtained recombinant DNA was deciphered by a DNA sequencer. In this manner, an internal sequence of the *Chionoecetes opilio* DSN gene 3' region was determined.

(3) Preparation of *Chionoecetes opilio* DSN Gene 5' Region Sequence

Nucleotide sequence of a 5' region of the *Chionoecetes opilio* DSN gene was deciphered by a 5' RACE method shown in the following. The reaction was carried out using the reagents attached to 5' RACE System for Rapid Amplification of cDNA Ends, Version 2.0 (manufactured by Invitrogen). Based on the obtained internal sequence of the *Chionoecetes opilio* DSN gene, M5RT (SEQ ID NO:9), M5R1 (SEQ ID NO:10) and M5R2 (SEQ ID NO:11) were prepared.

A cDNA was synthesized by the reverse transcription reaction shown below. As the template, 1 µg (0.5 µl) portion of the total RNA extracted from the *Chionoecetes opilio* hepatopancreas was used. After mixing 0.5 portion of the total RNA, 2.5 µl of the primer M5RT (SEQ ID NO:9) (1 µM) and 12.5 µl of the RNA Free H$_2$O, incubation was carried out at 70° C. for 10 minutes, followed by quick cooling on ice. As a reaction buffer, 2 µl of a 10 times concentration of a buffer (10×PCR buffer) was added to the mixed liquid after heat treatment (15.5 µl). Each of dNTP was added thereto to be a final concentration of 0.4 mM, and MgCl$_2$ was added to be a final concentration of 2.5 mM, and DTT to 10 mM, respectively, and the mixture was incubated at 42° C. for 1 minute. As the transcriptase, 200 U of SuperScript™ II Reverse Transcriptase was added thereto to prepare a reaction liquid (25 µl in total volume). The reaction liquid was incubated at 42° C. for 50 minutes and then incubated at 70° C. for 15 minutes to complete the transcription reaction. This reaction liquid was mixed with 1 µl of the RNAase mix and incubated at 37° C. for 30 minutes, and then the thus synthesized cDNA was purified using the S.N.A.P. column attached to said kit and eluted with 50 µl of sterile ultrapure water. Procedure of the purification operation was carried out in accordance with the technical specification attached to said kit.

Next, a TdT-tailing reaction was carried out. As the oligo-dC addition enzyme, Terminal deoxynucleotidyl transferase (TdT) attached to said kit was used. A mixed liquid (24 µl in total volume) was prepared by adding 10 µl of the S.N.A.P.-purified cDNA, 5 µl of a 5 times concentration of a buffer (5× tailing buffer) as the reaction buffer, and dCTP to be a final concentration of 0.2 mM. This mixed liquid was incubated at 94° C. for 3 minutes and rapidly cooled on ice. A reaction liquid (25 µl in total volume) was prepared by adding 1 µl of TdT and incubated at 37° C. for 10 minutes. Thereafter, TdT was inactivated by incubating at 65° C. for 10 minutes. This solution was used as dC-tailed cDNA solution.

A 5' region sequence of the *Chionoecetes opilio* DSN gene was amplified by the following PCR. As the template, 5 µl of the dC-tailed cDNA was used and added to a reaction liquid (50 µl in total volume). As the DNA polymerase, 2.5 U of TaKaRa Taq (manufactured by TAKARA BIO) was added to the reaction liquid. As the reaction buffer, 5 µl of 10 times concentration of a buffer liquid (10×PCR buffer) was added thereto. As the primers, M5R1 (SEQ ID NO:10) and AAP (SEQ ID NO:15) were respectively added to the reaction liquid to be a final concentration of 0.4 µM. Each of dNTP was added to the reaction liquid to be a final concentration of 0.2 mM, and MgCl$_2$ was added to be a final concentration of 1.5 mM, respectively. As the thermal cycler, Gene Amp PCR System 9600 (manufactured by Perkin Elmer) was used. An amplification product (D) was obtained by carrying out a heat treatment of 94° C. for 2 minutes once, and subsequently repeating 35 times of a temperature cycle consisting of 94° C. for 60 seconds, 55° C. for 30 seconds and 72° C. for 2 minutes.

Next, the amplification product (D) was diluted 100 times with sterile ultrapure water, and nested PCR was carried out using this diluted liquid as the template. As the template, 2 µl portion of the diluted liquid was used and added to a reaction liquid (50 µl in total volume). As the DNA polymerase, 2.5 U of TaKaRa Taq (manufactured by TAKARA BIO) was added to the reaction liquid. As the reaction buffer, 5 µl of 10 times concentration of a buffer liquid (10×PCR buffer) was added thereto. As the primers, M5R2 (SEQ ID NO:11) and AUAP (SEQ ID NO:14) were respectively added to the reaction liquid to be a final concentration of 0.2 µM. Each of dNTP was added to the reaction liquid to be a final concentration of 0.2 mM, and MgCl$_2$ to be a final concentration of 1.5 mM, respectively. A heat treatment was carried out once at 94° C. for 2 minutes, and subsequently a temperature cycle consisting of 94° C. for 60 seconds, 58° C. for 30 seconds and 72° C. for 3 minutes was repeated 35 times. The amplified products were subjected to an agarose gel electrophoresis, and a PCR amplification product of about 700 by (FIG. 1(d) lane 5') was recovered from the agarose gel using MinElute Gel Extraction Kit (manufactured by QIAGEN) and then purified and eluted with 10 µl of sterile ultrapure water. Procedure of the purification operation was carried out in accordance with the technical specification attached to said purification kit.

Using Mighty TA-cloning Kit (manufactured by TAKARA BIO), the thus obtained product was inserted into a pMD20-T vector attached to said kit. Procedure of this operation was carried out in accordance with the technical specification attached to said kit. Nucleotide sequence of the thus obtained recombinant DNA was deciphered by a DNA sequencer. In the above-mentioned manner, nucleotide sequence of the *Chionoecetes opilio* DSN gene 5' region was determined. Thus, nucleotide sequence of complete length mRNA of the *Chionoecetes opilio* DSN gene (SEQ ID NO:20) was finally obtained. Said sequence was possessed of the DSN gene of SEQ ID NO:1 which encodes a protein consisting of the amino acid sequence described in SEQ ID NO:2.

EXAMPLE 3

Cloning of *Chionoecetes opilio* DSN Complete Length Gene

Thus, we have determined the cDNA nucleotide sequence (SEQ ID NO:20) from the nucleotide sequence of mRNA of the *Chionoecetes opilio* DSN by Example 2, and then *Chionoecetes opilio* DSN complete length gene (SEQ ID NO:1) was cloned by designing primers MWF 1 (SEQ ID NO:12) and MWR 1 (SEQ ID NO:13). An electrophoresis image of the complete length gene is shown in FIG. 1(e).

Reverse transcription and PCR reactions were carried out using ReverTra-Plus-™ (manufactured by TOYOBO). Firstly, a cDNA was synthesized by the reverse transcription reaction shown below. A 1 µg (0.5 µl) portion of total RNA extracted from the *Chionoecetes opilio* hepatopancreas was used as the template. After mixing 0.5 µl of the total RNA, 5 µl of an oligo(dT) 20 primer (SEQ ID NO:17) (10 µM) and 6.5 µl of the RNase Free H$_2$O, a heat treatment at 65° C. for 5 minutes was carried out and then quick cooling on ice was carried out. As a reaction buffer, 4 µl of 5 times concentration of a buffer liquid (5×RT buffer) was added to the mixed liquid after heat treatment (12 µl). Thereto, 1 µl of RNase Inhibitor, 2 µl of each of 10 mM dNTP and 1 µl of ReverTra Ace (TOYOBO) as a reverse transcriptase were respectively added to prepare a reaction liquid (20 µl in total volume). The reaction liquid was incubated at 42° C. for 60 minutes and then incubated at 85° C. for 5 minutes to complete the reverse transcription reaction. This solution was used as a reverse transcription cDNA solution.

As the template, 2 µl of this reverse transcription cDNA was used and added to a reaction liquid (50 µl in total volume). As the DNA polymerase, 1.0 U of KOD plus (manufactured by TOYOBO) was added to the reaction liquid. As the reaction buffer, 5 µl of the 10 times concentration buffer liquid (10×PCR buffer) attached to the ReverTra-Plus-™ product was added thereto. Primers MWF 1 (SEQ ID NO:12) and MWR 1 (SEQ ID NO:13) were respectively added to the reaction liquid to be a final concentration of 0.3 µM. Each of dNTP was added to the reaction liquid to be a final concentration of 0.2 mM, and MgSO$_4$ was added to be a final concentration of 1.5 mM, respectively. As a thermal cycler, Gene Amp PCR System 9600 (manufactured by Perkin Elmer) was used. A heat treatment was carried out once at 94° C. for 2 minutes, and subsequently a temperature cycle consisting of 98° C. for 10 seconds, 57° C. for 30 seconds and 68° C. for 90 seconds was repeated 35 times. The amplified products were subjected to an agarose gel electrophoresis, and a PCR amplification product of about 1300 by (FIG. 1(e) lane F) was recovered from the agarose gel using MinElute Gel Extraction Kit (manufactured by QIAGEN) and then purified and eluted with 20 µl of sterile ultrapure water. Procedure of the purification operation was carried out in accordance with the technical specification attached to said purification kit. The thus obtained amplification product was inserted into a pUC18 vector in accordance with the general method. Nucleotide sequence of the thus obtained recombinant DNA (to be referred to as pUC18 ZDSN hereinafter) was deciphered using a DNA sequencer. In the above manner, the *Chionoecetes opilio* DSN complete length gene was cloned and its complete sequence was confirmed.

Coding region of the isolated *Chionoecetes opilio* DSN cDNA was a sequence consisting of 1215 bases (SEQ ID NO:1) and encoded a polypeptide consisting of a sequence of 404 amino acids (SEQ ID NO:2). The *Chionoecetes opilio* DSN showed a homology of 64% at the nucleotide sequence level, and 59% at the amino acid sequence level, with the *Penaeus japonicus* DNase (*Biochem J*, 346 Pt 3, 799-804 (2000)) and showed a homology of 66% at the nucleotide sequence level, and 61% at the amino acid sequence level, with the *Paralithodes camtschaticus* DSN (Expression of duplex-specific nuclease derived from *Paralithodes camtschaticus* by insect cells-baculovirus system. Eleventh Annual Meeting of Japanese Society for Marine Biotechnology P4-1(May 24 to May 25 in 2008)).

Figure 2:
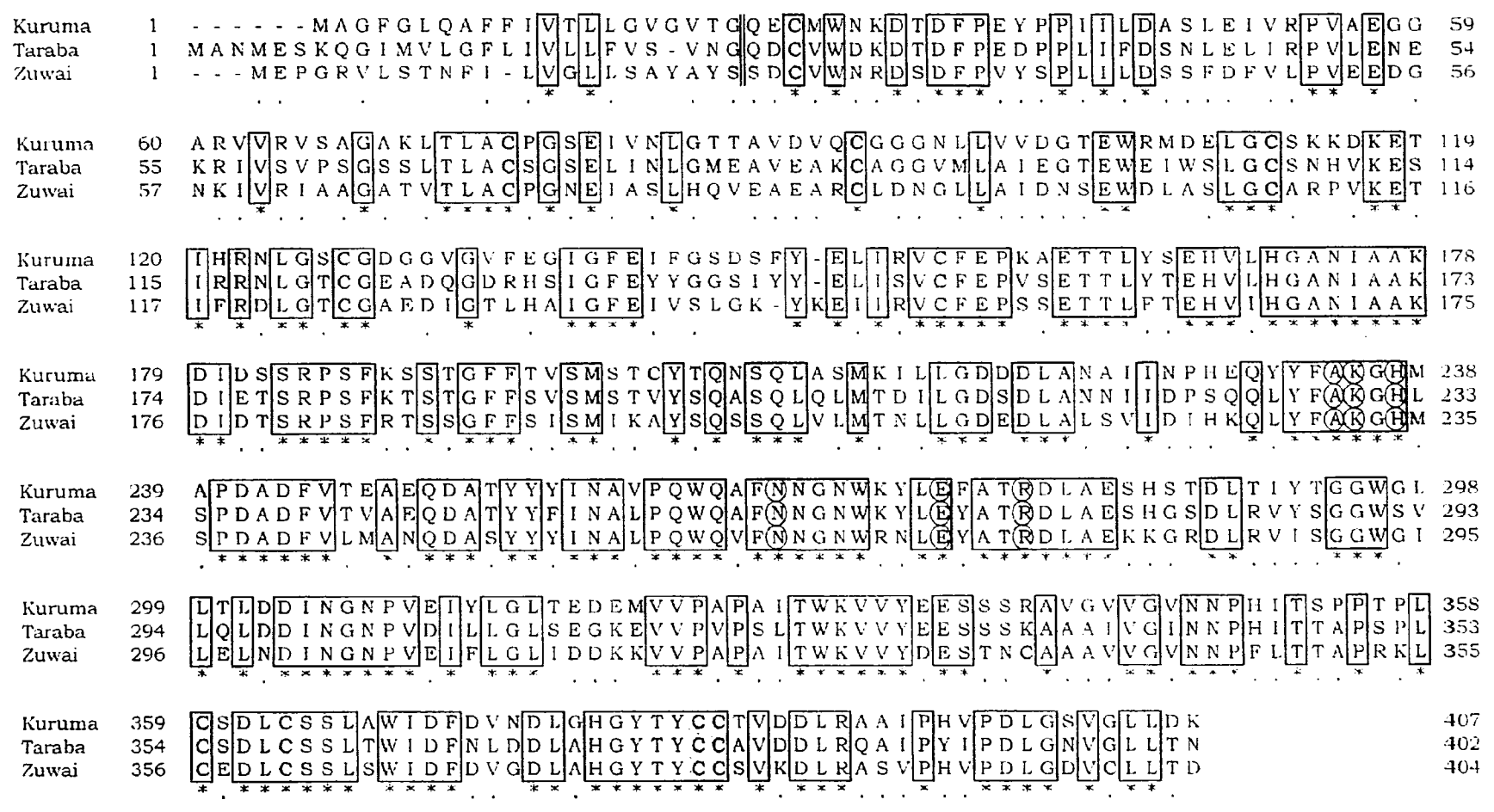

A multiple alignment showing comparison of amino acid sequences of *Chionoecetes opilio* DSN, *Penaeus japonicus* DNase and *Paralithodes camtschaticus* DSN is shown in FIG. 2. In FIG. 2, Kuruma represents an amino acid sequence of *Penaeus japonicus* DNase, and Taraba represents an amino acid sequence of *Paralithodes camtschaticus* DSN and Zuwai represents an amino acid sequence of *Chionoecetes opilio* DSN. Amino acids coincided within the three sequences were shown by enclosing with a square. The signal peptide cut site was shown by a vertical double line (∥). The signal peptide cut sites of *Chionoecetes opilio* DSN and *Paralithodes camtschaticus* DSN are cut sites estimated by the SignalP 3.0 software (*J. Mol. Biol.*, 340, 783-95, 2004), and the signal peptide cut site of *Penaeus japonicus* DNase is a cut site revealed by a test of Wang et al. (*Biochem J*, 346 Pt 3, 799-804(2000)). The amino acid residues of positions which correspond to the active sites of NUC preservation domain of the DNA/RNA-nonspecific endonuclease family are shown by open circles (◯). Cys residues in the sequences are shown by gray. The *Chionoecetes opilio* DSN has a presumed signal sequence of 23 amino acids starting from the N-terminal. Calculated molecular weight of the complete length polypeptide was 44.3 kDa and its estimated isoelectric point was 4.4. Calculated molecular weight of estimated mature polypeptide was 41.8 kDa and its estimated isoelectric point was 4.4. The *Chionoecetes opilio* DSN was possessed of a total of 12 Cys residues, including 10 Cys residues presenting at positions preserved between it and the *Paralithodes camtschaticus* DSN and 2 further additional Cys residues.

EXAMPLE 4

Expression and Purification of Recombinant *Chionoecetes opilio* DSN

Using the *Chionoecetes opilio* DSN cDNA isolated by Example 3, expression and purification of a recombinant DSN enzyme in a baculovirus-insect cell system were carried out.

(1) Preparation of Recombinant Baculovirus

The *Chionoecetes opilio* DSN cDNA was amplified by the PCR shown below. In order to insert the *Chionoecetes opilio* DSN cDNA into an insect cell expression vector pVL1393, primers MEPF (SEQ ID NO:18) and MEPR-His (SEQ ID NO:19) were prepared. In order to effect expression of the *Chionoecetes opilio* DSN as a C-terminal His-tag fusion protein, a nucleotide sequence coding for 6× histidine (SEQ ID NO: 22) was added to the 5' end side of the MEPR-His (SEQ ID NO:19).

As the template, 6 ng portion of the pUC18 ZDSN prepared in Example 3 was used and added to a reaction liquid (50 µl in total volume). As the DNA polymerase, 1.0 U of KOD plus (manufactured by TOYOBO) was added to the reaction liquid. As the reaction buffer, 5 µl of the 10 times concentration buffer liquid (10×KOD-PCR buffer) attached to the KOD plus product was added thereto. As primers, MEPF (SEQ ID NO:18) and MEPR-His (SEQ ID NO:19) were respectively added to the reaction liquid to be a final concentration of 0.3 µM. Each of dNTP was added to the reaction liquid to be a final concentration of 0.2 mM, and $MgSO_4$ to be a final concentration of 1.5 mM, respectively. As a thermal cycler, Gene Amp PCR System 9600 (manufactured by Perkin Elmer) was used. A heat treatment was carried out once at 94° C. for 2 minutes, and subsequently a temperature cycle consisting of 94° C. for 15 seconds, 57° C. for 30 seconds and 68° C. for 90 seconds was repeated 35 times. When the amplification product was verified by an agarose gel electrophoresis, a band was confirmed at a position of about 1250 bp. The PCR amplification product was purified using MinElute PCR Purification Kit (manufactured by QIAGEN) and eluted with 50 µl of sterile ultrapure water. Procedure of the purification operation was carried out in accordance with the technical specification attached to said purification kit. The thus purified amplification product was digested using EcoRI (manufactured by Nippon Gene) and BamHI (manufactured by Nippon Gene) and then purified using MinElute PCR Purification Kit (manufactured by QIAGEN) and eluted with 20 µl of sterile ultrapure water. The amplification product digested with restriction enzymes was inserted into a pVL1393 vector in accordance with a general method. Nucleotide sequence of the thus obtained recombinant DNA (to be referred to as pVL1393 ZDSN-His hereinafter) was deciphered by a DNA sequencer to confirm that it coincides with that of SEQ ID NO:1.

A solution A (50 µl in total volume) was prepared by mixing 2 µg of the thus prepared pVL1393 ZDSN-His, 0.5 µg of Sapphire Baculovirus DNA (manufactured by Orbigen) and a serum-free medium Sf-900 II SFM (manufactured by Invitrogen). Also, a solution B was prepared by mixing 45 µl of the Sf-900 II SFM and 5 µl of Cellfectin Reagent (manufactured by Invitrogen). A solution C was prepared by mixing the solution A and solution B and allowed to stand still at room temperature for 30 minutes. The solution C was added to a *Spodoptera frugiperda*-derived Sf9 cell (manufactured by Invitrogen) which had been prepared in a dish of 60 mm in diameter to be a density of $0.4 \times 10^6$ cells/ml (4 ml in total volume), and the cells were incubated at 28° C. for 6 hours. By discarding the medium alone, 3 ml of fresh Sf-900 II SFM was added and incubated at 28° C. for 5 days. The virus-infected culture medium was centrifuged at 2,500×rpm for 10 minutes, and the supernatant was recovered. This supernatant was used as a 1st recombinant virus liquid. Next, in order to increase infection potency of the recombinant virus, the following operation was carried out. To be a density of $0.5 \times 10^6$ cells/ml (15 ml in total volume), 500 µl portion of the 1st recombinant virus liquid was added to the Sf9 cell which had been prepared in a tissue culture flask (manufactured by Nunc), and incubated at 28° C. for 5 days. The virus-infected culture medium was centrifuged at 2,500×rpm for 10 minutes to recover the supernatant. This supernatant was used as a 2nd recombinant virus liquid. Next, 1 ml of the thus prepared 2nd recombinant virus liquid was added to expresSF+ (manufactured by Protein Science) which had been prepared in a conical flask equipped with a bent cap (manufactured by Corning) to a density of $1.0 \times 10^6$ cells/ml (50 ml in total volume), and incubated at 28° C. for 4 days with shaking. The virus-infected culture medium was centrifuged at 2,500×rpm for 10 minutes to recover the supernatant. This supernatant was used as a 3rd recombinant virus liquid.

(2) Expression and Purification of Recombinant *Chionoecetes opilio* DSN

Figure 3:
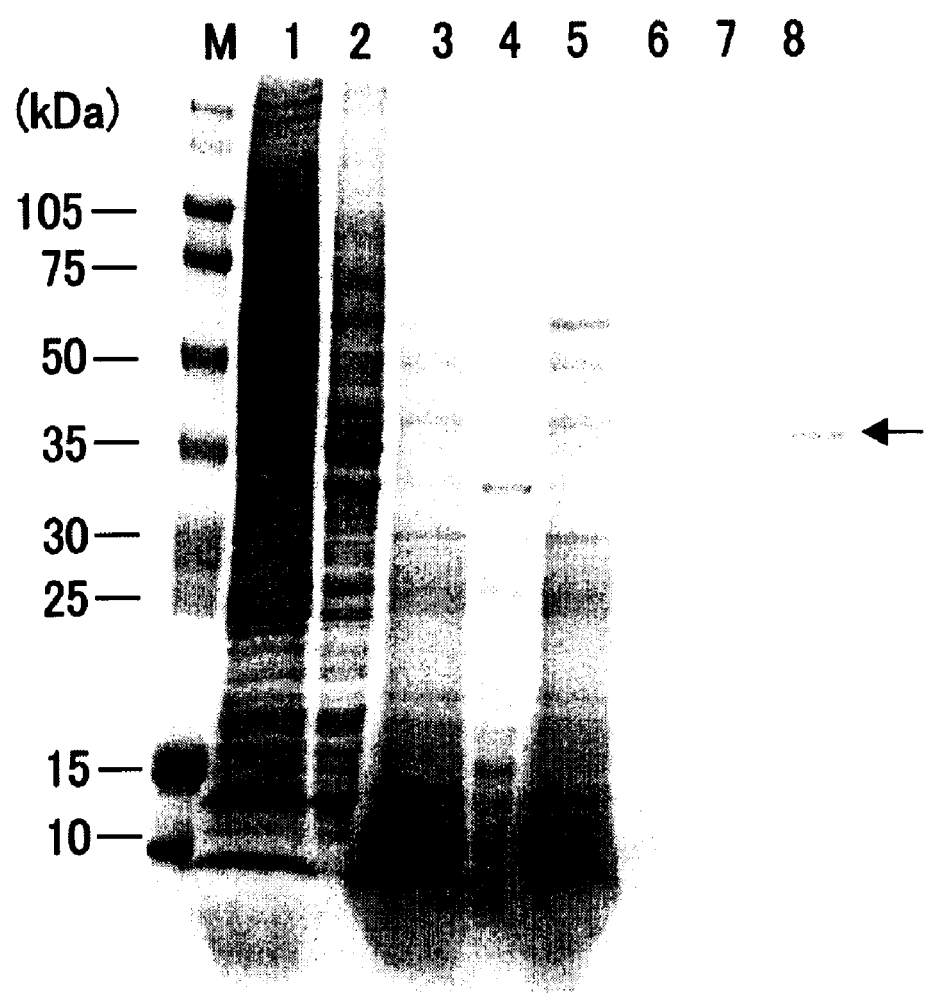
FIG. 3 is a figure showing SDS-PAGE of each fraction of the purification steps of *Chionoecetes* (snow crab) DSN.

Expression and purification of recombinant *Chionoecetes opilio* DSN were carried out in accordance with the following procedure. To be a density of $1.0 \times 10^6$ cells/ml (100 ml in total volume), 1 ml portion of the thus prepared 3rd recombinant virus liquid was added to Sf9 cell which had been prepared in a conical flask equipped with a bent cap (manufactured by Corning), and incubated at 28° C. for 4 days with shaking. The infection was further carried out in 2 said flasks (300 ml in total) under the same conditions. The virus-infected culture medium (300 ml in total volume) was centrifuged at 2,500× rpm for 10 minutes. The thus precipitated cells were suspended in 20 ml of a buffer A (20 mM $NaH_2PO_4$ (pH 7.4), 500 mM NaCl, 10 mM imidazole, 10% glycerol, 5 mM 2-mercaptoethanol, 0.2% NP 40) and allowed to stand still on ice for 1 hour. The suspension was subjected to ultrasonic disintegration and then centrifuged at 7,000 rpm for 20 minutes to recover the supernatant. Proteinase K (manufactured by TAKARA BIO) was added to the thus obtained supernatant to be a final concentration of 20 µg/ml and incubated at 37° C. for 30 minutes to effect degradation of the insect cells and baculovirus-derived protein contained in the supernatant. This treated liquid was centrifuged at 7,000×rpm for 20 minutes to recover the supernatant. The *Chionoecetes opilio* DSN was purified from the thus obtained supernatant using TALON metal affinity resin (manufactured by Clontech). As buffers in this case, a buffer B (20 mM $NaH_2PO_4$ (pH 7.4), 500 mM NaCl, 10 mM imidazole, 10% glycerol, 5 mM 2-mercaptoethanol) was used for the washing of TALON, and a buffer C (20 mM $NaH_2PO_4$ (pH 7.4), 500 mM NaCl, 500 mM imidazole, 10% glycerol, 5 mM 2-mercaptoethanol) was used for the elution. A SDS-PAGE was carried out on the thus obtained elution fractions. The results are shown in FIG. 3. In FIG. 3, respective lanes represent the following samples: lane M; molecular weight markers, lane 1; cell disintegration supernatant, lane 2; cell integration precipitate, lane 3; proteinase K treated supernatant, lane 4; proteinase K treated precipitate, lane 5; TALON non-adsorption fraction, lane 6; TALON washing fraction 1, lane 7; TALON washing fraction 2, lane 8; imidazole elution fraction. As a result of this, it was confirmed that a single protein band which coincides with the presumed molecular weight of the *Chionoecetes opilio* DSN is observed (lane 8 in FIG. 3, the band considered to be the *Chionoecetes opilio* DSN is shown by an arrow). By the above purification operation, about 50 µg of the high purity enzyme was obtained from 300 ml of the virus-infected culture medium.

(3) Effects of Proteinase K Treatment and Heat Treatment on Purification Purity of *Chionoecetes opilio* DSN Effects of proteinase K treatment and heat treatment on the purification purity of *Chionoecetes opilio* DSN were examined. The purification purities were compared in accordance with the following procedure. To expresSF+ cell which had been prepared in a conical flask equipped with a bent cap (manufactured by Corning), 1 ml of the 2nd recombinant virus liquid prepared in Example 4(1) was added to be a density of $1.0 \times 10^6$ cells/ml (50 ml in total volume), and incubated at 28° C. for 4 days with shaking. The virus-infected culture medium (50 ml in total volume) was centrifuged at 2,500×rpm for 10 minutes. The thus precipitated cells were suspended in 4 ml of the buffer A (20 mM $NaH_2PO_4$ (pH 7.4), 500 mM NaCl, 10 mM imidazole, 10% glycerol, 5 mM 2-mercaptoethanol, 0.2% NP 40) and allowed to stand still on ice for 1 hour. This suspension was subjected to ultrasonic disintegration and then centrifuged at 7,000 rpm for 20 minutes to recover the supernatant. The thus obtained supernatant was recovered in 2 ml portions into separate containers. Proteinase K (manufactured by TAKARA BIO) was added to one of the containers to be a final concentration of 20 µg/ml, incubated at 37° C. for 30 minutes and then treated at 60° C. for 15 minutes. The treated liquid was centrifuged at 15,000× rpm for 20 minutes to recover the supernatant (treated supernatant). These treatments were not carried out on the other container (untreated supernatant). The *Chionoecetes opilio* DSN was purified from each of the treated supernatant and untreated supernatant using TALON metal affinity resin (manufactured by Clontech). As buffers in this case, the buffer B (20 mM $NaH_2PO_4$ (pH 7.4), 500 mM NaCl, 10 mM imidazole, 10% glycerol, 5 mM 2-mercaptoethanol) was used for the washing of TALON, and the buffer C (20 mM $NaH_2PO_4$ (pH 7.4), 500 mM NaCl, 500 mM imidazole, 10% glycerol, 5 mM 2-mercaptoethanol) was used for the elution.

Figure 4:
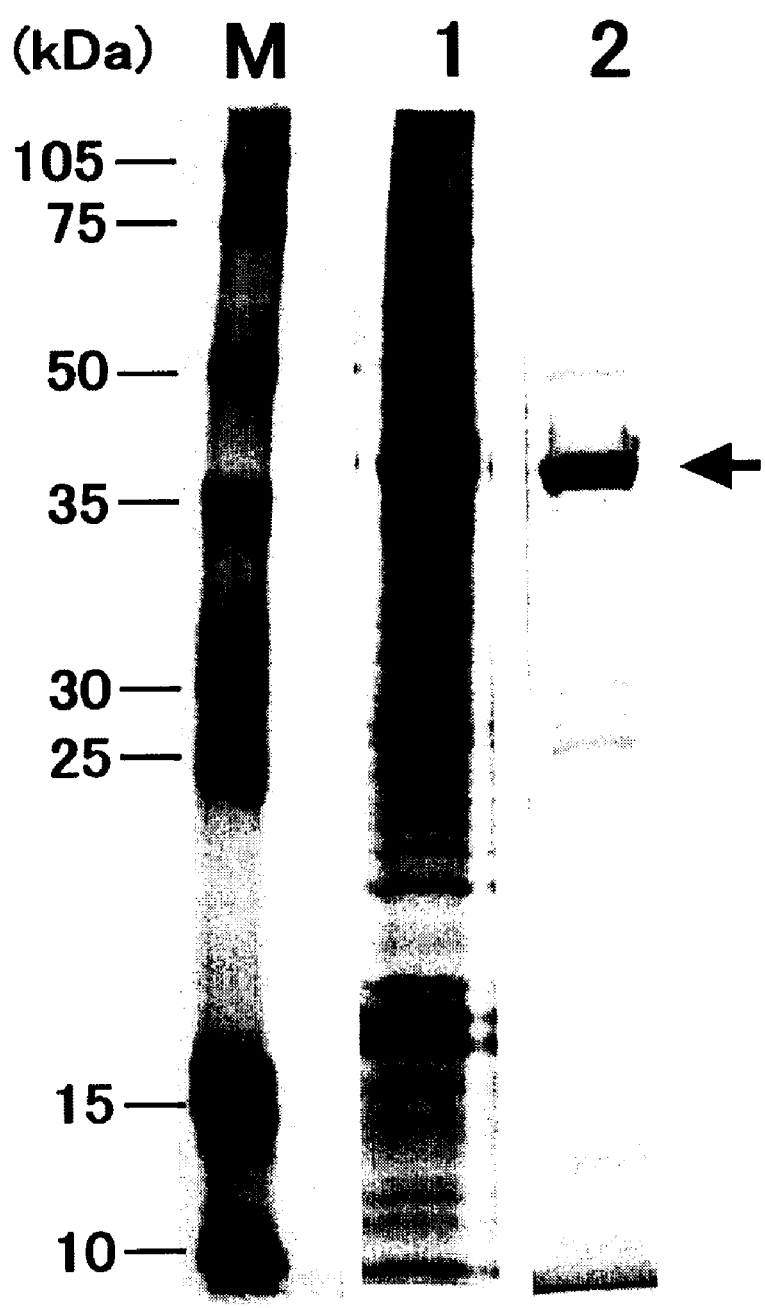
FIG. 4 is a figure showing effects of proteinase K treatment and heat treatment in the purification of *Chionoecetes* (snow crab) DSN.

SDS-PAGE was carried out on each of the thus obtained elution fractions. A result of this are shown in FIG. 4. In FIG. 4, the samples added to respective lanes are as follows: lane M; molecular weight markers, lane 1; elution fraction when the proteinase K treatment and heat treatment were not carried out (10 µl), lane 2; elution fraction when the proteinase K treatment and heat treatment were carried out (10 µl). In the lane 1, although a band which coincides with the presumed molecular weight of the *Chionoecetes opilio* DSN was observed at the position shown by an arrow, a large number of bands other than this were present. On the other hand, an almost single band considered to be said DSN was observed in the lane 2. Additionally, it was observed that light or shade of the band which corresponds to said DSN presenting in each elution fraction was the same between lane 1 and lane 2. Namely, it is considered that the proteinase K treatment and heat treatment do not exert influence on the purification yield of the *Chionoecetes opilio* DSN. The fact indicates that the insect cell and baculovirus-derived protein are degraded or precipitated by said treatments while the *Chionoecetes opilio* DSN is not degraded or precipitated. Thus, said treatments are effective as purification step of the *Chionoecetes opilio* DSN expressed using the insect cell-baculovirus system. Additionally, the purification method of DSN shown by Example 4(2) is a method by which the *Chionoecetes opilio* DSN can be obtained easily and with high purity through two steps of the proteinase K treatment and affinity purification, without requiring a procedure of solubilizing and refolding insolubilized inclusion bodies.

EXAMPLE 5

Duplex-specific Nuclease Activity of *Chionoecetes opilio* DSN (1) DNase Activity of *Chionoecetes opilio* DSN DNase activity of the *Chionoecetes opilio* DSN purified enzyme obtained in Example 4 was measured. A bovine thymus-derived DNA (manufactured by Wako Pure Chemical Industries) was used as the substrate. The activity measurement was carried out in accordance with the Kunitz method (Kunitz, M., J. Gen. Physiol., 33, 349-362, 1950). The reaction substrate solution was prepared by adding the bovine thymus-derived DNA to 50 mM Tris-HCl (pH 8.0) and 7 mM $MgCl_2$, to be a final concentration of 40 µg/ml. The thus prepared reaction substrate solution (990 µl) was added to a quartz cell and equilibrated at 25° C. Thereto, 10 µl of the purified enzyme was added and quickly stirred, and then the absorbance at a wavelength of 260 nm was measured at every 5 seconds. The enzyme activity which increases the absorbance at a wavelength of 260 nm by a factor of 0.001 during 1 minute was regarded as 1 U. As a result of this, it was shown that the activity of the purified enzyme is 1,313 U/ml.

(2) Duplex-specific Nuclease Activity of *Chionoecetes opilio* DSN

Figure 5:
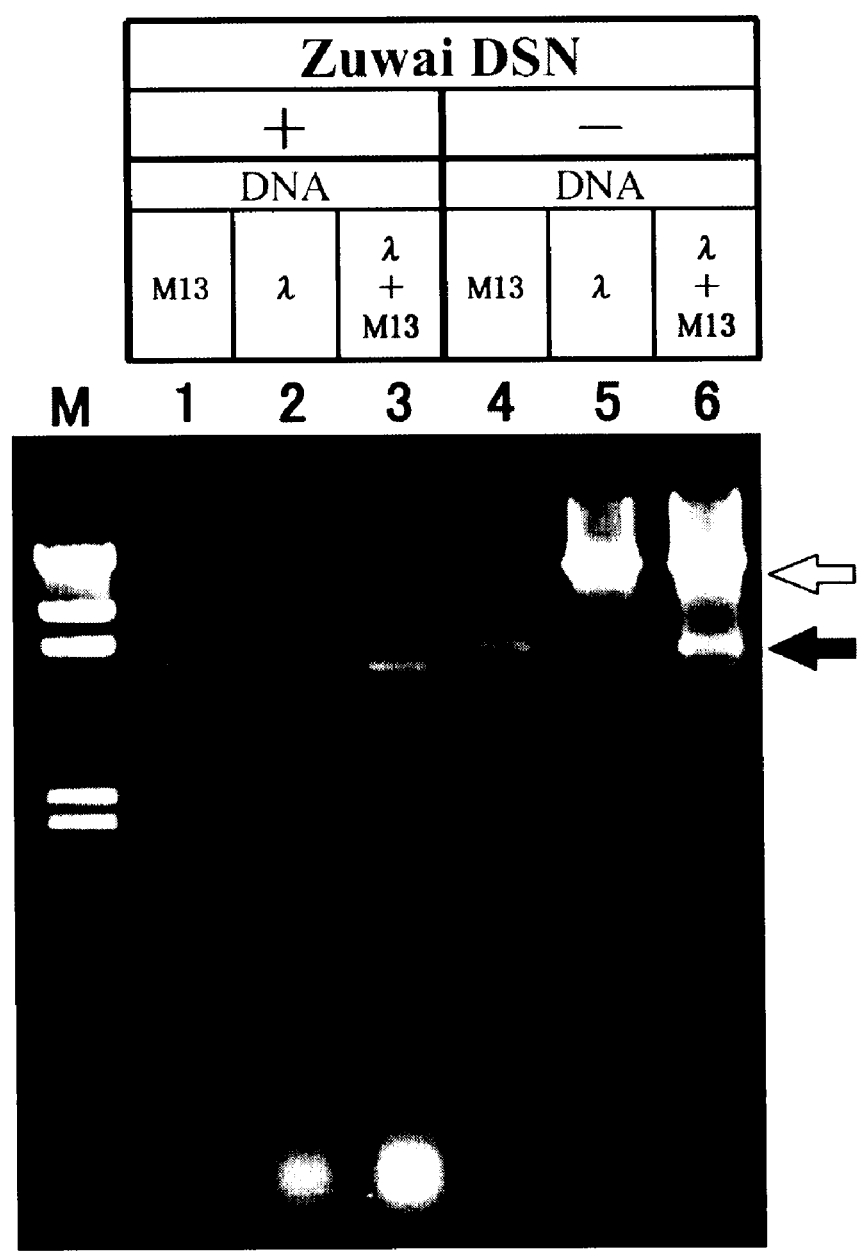
FIG. 5 is a figure showing duplex-specific nuclease activity of *Chionoecetes* (snow crab) DSN.

Duplex-specific nuclease activity of *Chionoecetes opilio* DSN was evaluated. A λ DNA (manufactured by Nippon Gene) was used as the double-stranded DNA substrate, and the M13 mp 18 single strand DNA (manufactured by TAKARA BIO) was used as the single-stranded DNA substrate. The substrate solution was prepared by adding λ DNA and M13 mp18 single strand DNA to 50 mM Tris-HCl (pH 8.0) and 7 mM $MgCl_2$, to be respective final concentrations of 21 µg/ml and 10 µg/ml. Additionally, substrate solutions to which the DNA substrates were separately added were also prepared. A reaction liquid was prepared by adding 1 µl (0.5 U) of the *Chionoecetes opilio* DSN purified enzyme to 9 µl of each substrate solution. Separately, a sample to which 1 µl of the buffer B of Example 4 was added instead of the enzyme was prepared as a negative control. The thus prepared reaction liquid was incubated at 60° C. for 3 minutes. After completion of the reaction, a 10 µl portion of the reaction liquid was subjected to 1.0% agarose gel electrophoresis and stained with SYBR Green II (manufactured by TAKARA BIO), and then the presence or absence and light or shade of respective substrate bands were compared under UV irradiation. The electrophoresis images are shown in FIG. 5. In FIG. 5, lane M is λ/Hind III digest DNA size marker (manufactured by TOYOBO). The samples which contain the enzyme are lanes 1 to 3 (Zuwai DSN+). The samples which do not contain the enzyme are lanes 4 to 6 (Zuwai DSN−), and the substrate DNA added to the reaction liquid is shown on the upper side of each lane umber (M13, λ and M13+λ). Also in FIG. 5, the void arrow indicates the position of intact molecular weight of λ DNA, and the black arrow indicates the position of M13 DNA.

As a result of this, in the case of the enzyme-added reaction liquid (Zuwai DSN+; FIG. 5, lanes 1, 2 and 3), the double-stranded DNA substrate λ DNA (void arrow) alone was degraded, while the single-stranded DNA substrate M13 mp 18 single strand DNA (black arrow) was not degraded. On the other hand, when the buffer B was added instead of the enzyme (Zuwai DSN−; FIG. 5, lanes 4, 5 and 6), both of the substrate were not degraded. Based on this, although it was shown that the *Chionoecetes opilio* DSN hardly acts on the single-stranded DNA, it specifically degrades the double-stranded DNA alone.

EXAMPLE 6

Heat Resistance of *Chionoecetes opilio* DSN (1) Residual Activity after Heat Treatment Heat resistance of *Chionoecetes opilio* DSN was evaluated by the following method. A bovine thymus-derived DNA (manufactured by Wako Pure Chemical Industries) was used as the substrate. The activity measurement was carried out in accordance with the Kunitz method (*J. Gen. Physiol.*, 33, 349-362, 1950). The reaction substrate solution was prepared by adding the bovine thymus-derived DNA to 50 mM Tris-HCl (pH 8.0) and 7 mM $MgCl_2$, to be a final concentration of 40 µg/ml.

The thus prepared reaction substrate solution (990 µl) was added to a quartz cell and equilibrated at 25° C. The *Chionoecetes opilio* DSN purified enzyme obtained in Example 4 was incubated at each temperature of 50° C., 60° C., 63° C., 70° C. or 80° C. for 5, 10, 15, 20 or 30 minutes, and then a 10 µl portion thereof was added to the reaction substrate solution and quickly stirred. The absorbance at a wavelength of 260 nm was measured at every 5 seconds. The amount of the enzyme which increases the absorbance at a wavelength of 260 nm by a factor of 0.001 during 1 minute was regarded as 1 U.

Figure 6:
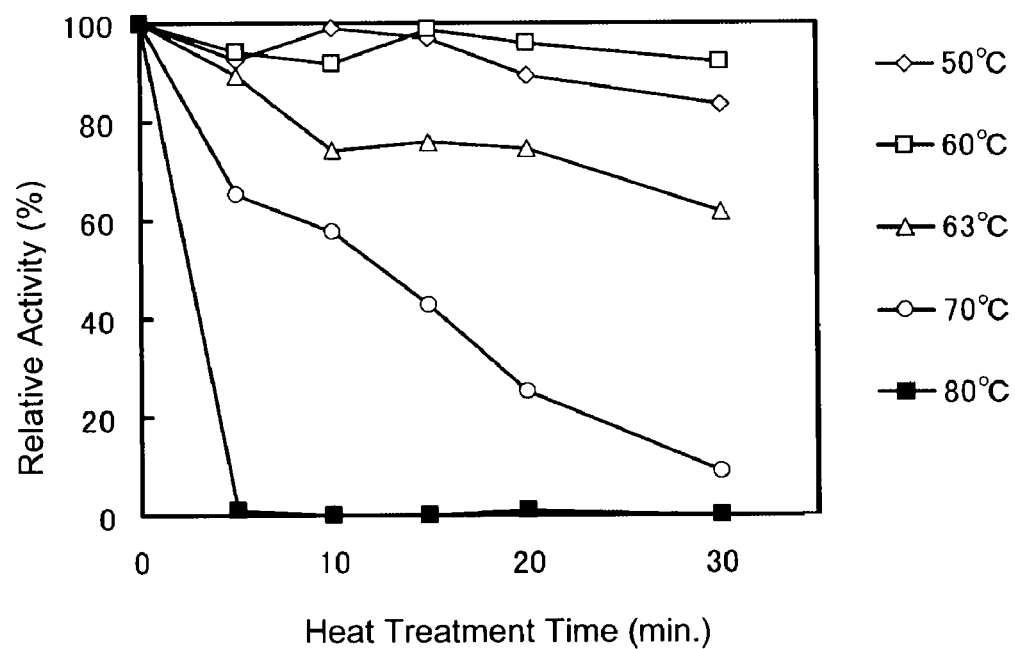
FIG. 6 is a figure showing residual activity of *Chionoecetes* (snow crab) DSN after heat treatment.

Changes in the relative activity (%) after the heat treatment based on the activity before the heat treatment are shown in FIG. 6. As a result, the enzyme treated at 50° C. or 60° C. maintained 80% or more of its activity of before the heat treatment even after a lapse of time of 30 minutes. The activity of the enzyme treated at 63° C. became lower than 80% of before the heat treatment after a lapse of time of 10 minutes. The activity of the enzyme treated at 70° C. decreased to be about 40% of before the heat treatment after a lapse of time of 15 minutes and decreased to be about 10% after a lapse of time of 30 minutes. The activity of the enzyme treated at 80° C. disappeared after 5 minutes. This result shows that the *Chionoecetes opilio* DSN has such a heat resistance that it can maintain its activity of higher than 80% by withstanding 30 minutes of heating at a temperature of at least up to 60° C.

(2) Optimum Activity Temperature

DNA degrading activity of the *Chionoecetes opilio* DSN at various temperatures was evaluated by the following method. A bovine thymus-derived DNA (manufactured by Wako Pure Chemical Industries) was used as the substrate. The reaction substrate solution was prepared by adding the bovine thymus-derived DNA to 50 mM Tris-HCl (pH 8.0) and 7 mM $MgCl_2$, to a final concentration of 40 µg/ml.

The thus prepared reaction substrate solution (990 µl) was added to a quartz cell and equilibrated at each activity measuring temperature of within the range of from 20° C. to 70° C. In order to prevent evaporation of the solution, a lidded quarts cell was used for the activity measurement. When the value of absorbance at a wavelength of 260 nm was stabilized, 10 µl of the *Chionoecetes opilio* DSN purified enzyme obtained in Example 4 was added thereto and quickly stirred. The absorbance at a wavelength of 260 nm was measured at every 5 seconds. The amount of the enzyme which increases the absorbance at a wavelength of 260 nm by a factor of 0.001 during 1 minute was regarded as 1 U of enzyme activity.

Figure 7:
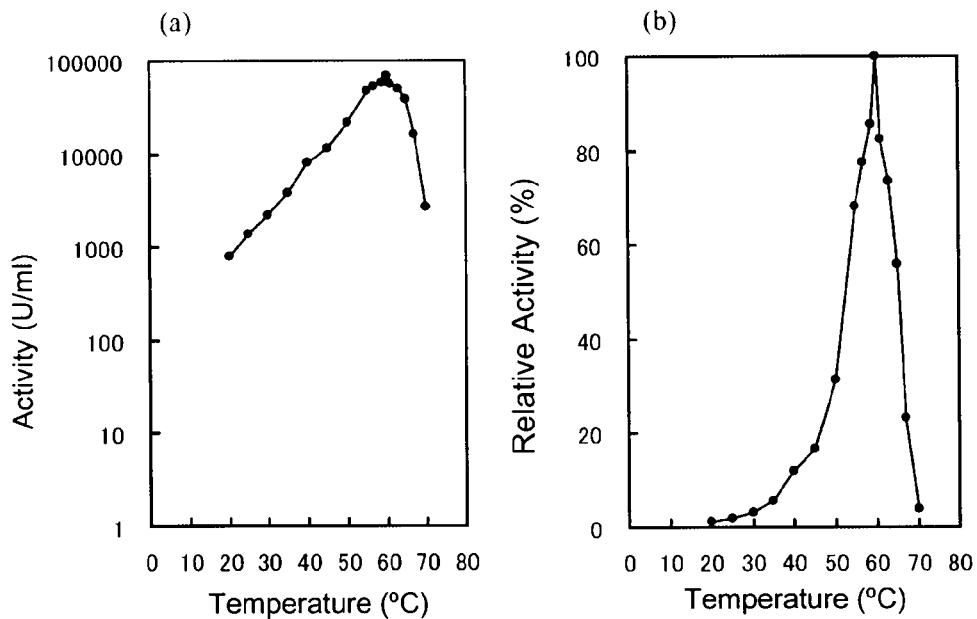
FIG. 7 is a figure showing optimum activity temperature of *Chionoecetes* (snow crab) DSN.

A result of the measurement is shown in FIG. 7. FIG. 7 is a graph showing (a) measured activity (U/ml) and (b) relative activity (%) at each temperature. Based on this result, it was found that the *Chionoecetes opilio* DSN shows high activity within the range of from about 20° C. (789 U/ml) to 63° C. (50,250 U/ml), its optimum activity temperature is about 60° C., and it shows an activity of 70% or more of the maximum activity at from about 55° C. to 63° C.

EXAMPLE 7

Metal Ion Requirement of *Chionoecetes opilio* DSN

Metal ion requirement of *Chionoecetes opilio* DSN was evaluated by the following method. A bovine thymus-derived DNA (manufactured by Wako Pure Chemical Industries) was used as the substrate. The activity measurement was carried out in accordance with the Kunitz method (*J. Gen. Physiol.*, 33, 349-362, 1950). The reaction substrate solution was prepared by adding 0, 1, 2, 3, 4, 5, 6, 7, 8, 9, 10, 12, 14, 16, 18, 20, 30, 40, 50 or 100 mM of each of $MgCl_2$, $MnCl_2$ and $CaCl_2$ to 50 mM Tris-HCl (pH 7.0), and by adding the bovine thymus-derived DNA to the solution to be a final concentration of 40 µg/ml.

Figure 8:
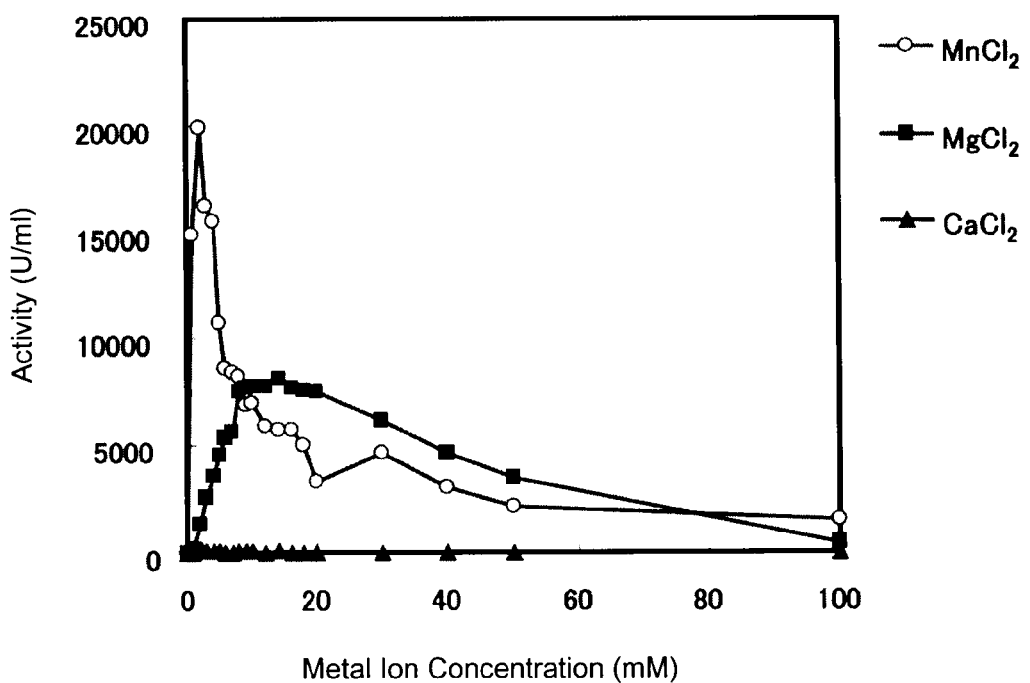
FIG. 8 is a figure showing metal ion requirement of *Chionoecetes* (snow crab) DSN.

The thus prepared each reaction substrate solution (990 µl) was added to a quartz cell and equilibrated at 25° C. Thereto, 10 µl of the *Chionoecetes opilio* DSN purified enzyme obtained in Example 4 was added and quickly stirred. The absorbance at a wavelength of 260 nm was measured at every 5 seconds. The amount of the enzyme which increases the absorbance at a wavelength of 260 nm by a factor of 0.001 during 1 minute was regarded as 1 U of the activity. A result of the measurement is shown in FIG. 8. FIG. 8 shows the activity (U/ml) measured at respective concentrations of $MgCl_2$, $MnCl_2$ and $CaCl_2$. This result shows that the *Chionoecetes opilio* DSN shows suitable activity in the presence of $Mg^{2+}$ ion or in the presence of $Mn^{2+}$ ion, but on the other hand, is insensitive to $Ca^{2+}$ ion.

EXAMPLE 8

Influence of Reaction Temperature Upon Single-stranded DNA Degradation by *Chionoecetes opilio* DSN Influence of reaction temperature upon the single-stranded DNA degradation by *Chionoecetes opilio* DSN was evaluated. M13 mp 18 single strand DNA (manufactured by TAKARA BIO) was used as the single-stranded DNA substrate. The substrate solution was prepared by adding M13 mp18 single strand DNA to 50 mM Tris-HCl (pH 8.0) and 7 mM $MgCl_2$, to be a final concentration of 10 µg/ml. A reaction liquid was prepared by adding 1 µl (0.5 U) of the *Chionoecetes opilio* DSN purified enzyme to 9 µl of the substrate solution. The thus prepared reaction liquid was incubated at each temperature of 30° C., 40° C., 50° C. and 60° C. for 0, 10 or 30 minutes. After completion of the reaction, 10 µl of the reaction liquid was subjected to 1.0% agarose gel electrophoresis, the gel was stained with SYBR Green II (manufactured by TAKARA BIO), and then the presence or absence and light or shade of each substrate band were compared.

Figure 9:
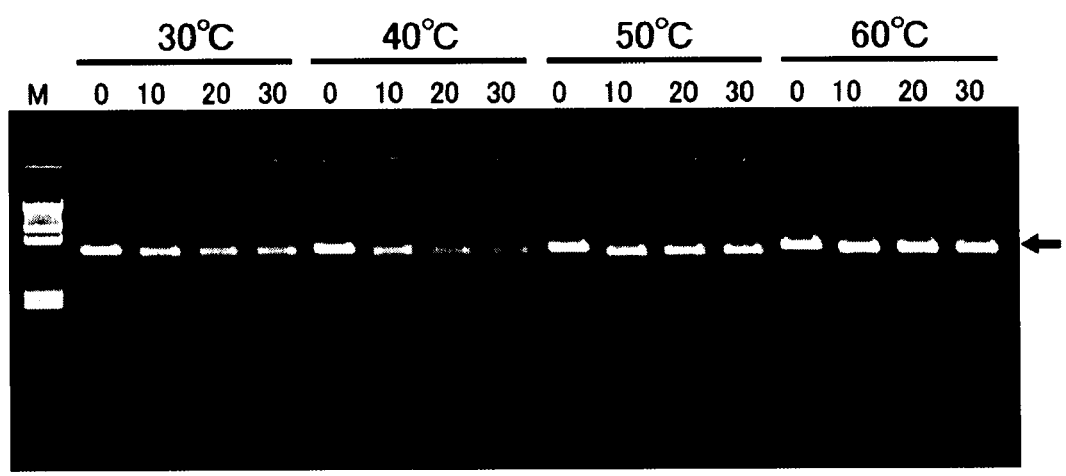
FIG. 9 is a figure showing influence of reaction temperature upon single-stranded DNA degradation of *Chionoecetes* (snow crab) DSN.

The thus obtained electrophoresis image is shown in FIG. 9. In FIG. 9, lane M is λ/Hind III digest DNA size marker (manufactured by TOYOBO), the numeral value on each lane represents the reaction time and the reaction temperature is shown further thereon. Additionally, the arrow in FIG. 9 indicates position of the intact molecular weight of M13 DNA. As a result of this, complete disappearance of the band of single-stranded DNA was not found at all of the temperatures tested even after a lapse of time of 30 minutes from the commencement of the reaction. This was in contrast to the fact that the *Chionoecetes opilio* DSN in the same amount of this Example (0.5 U) completely degraded a double-stranded DNA (λ DNA) by a reaction of merely 3 minutes in Example 5(2) (FIG. 5). That is, it was found from the results of this Example that, as shown in FIG. 9, the *Chionoecetes opilio* DSN has a considerably low activity to degrade single-stranded DNA, or does not have the degradation activity, within a broad range of temperature, and that this enzyme has a markedly high selectivity for double-stranded DNA. Additionally, it was found that the *Chionoecetes opilio* DSN has more high double-stranded nucleic acid selectivity at a temperature of 50° C. or more and has further high double-stranded nucleic acid selectivity at 60° C.

EXAMPLE 9

Influence of Reaction Temperature Upon Single-stranded DNA Degradation by *Chionoecetes opilio* DSN Under a Double-stranded DNA Coexisting Condition Influence of reaction temperature upon the single-stranded DNA degradation by *Chionoecetes opilio* DSN was evaluated under a double-stranded DNA coexisting condition. M13 mp18 single strand DNA (manufactured by TAKARA BIO) was used as the single-stranded DNA substrate, and λ DNA (manufactured by Nippon Gene) was used as the double-stranded DNA. The substrate solution was prepared by adding λ DNA and M13 mp18 single strand DNA to 50 mM Tris-HCl (pH 8.0) and 7 mM $MgCl_2$, to be respective final concentrations of 21 μg/ml and 10 μg/ml. A reaction liquid was prepared by adding 1 μl of the *Chionoecetes opilio* DSN purified enzyme to 9 μl of the substrate solution. The thus prepared reaction liquid was incubated at a temperature of 25° C. or 60° C. for 0, 3, 10 or 30 minutes.

After completion of the reaction, 10 μl of the reaction liquid was subjected to 1.0% agarose gel electrophoresis, the gel was stained with SYBR Green II (manufactured by TAKARA BIO), and then the presence or absence and light or shade of each substrate band were compared.

Figure 10:
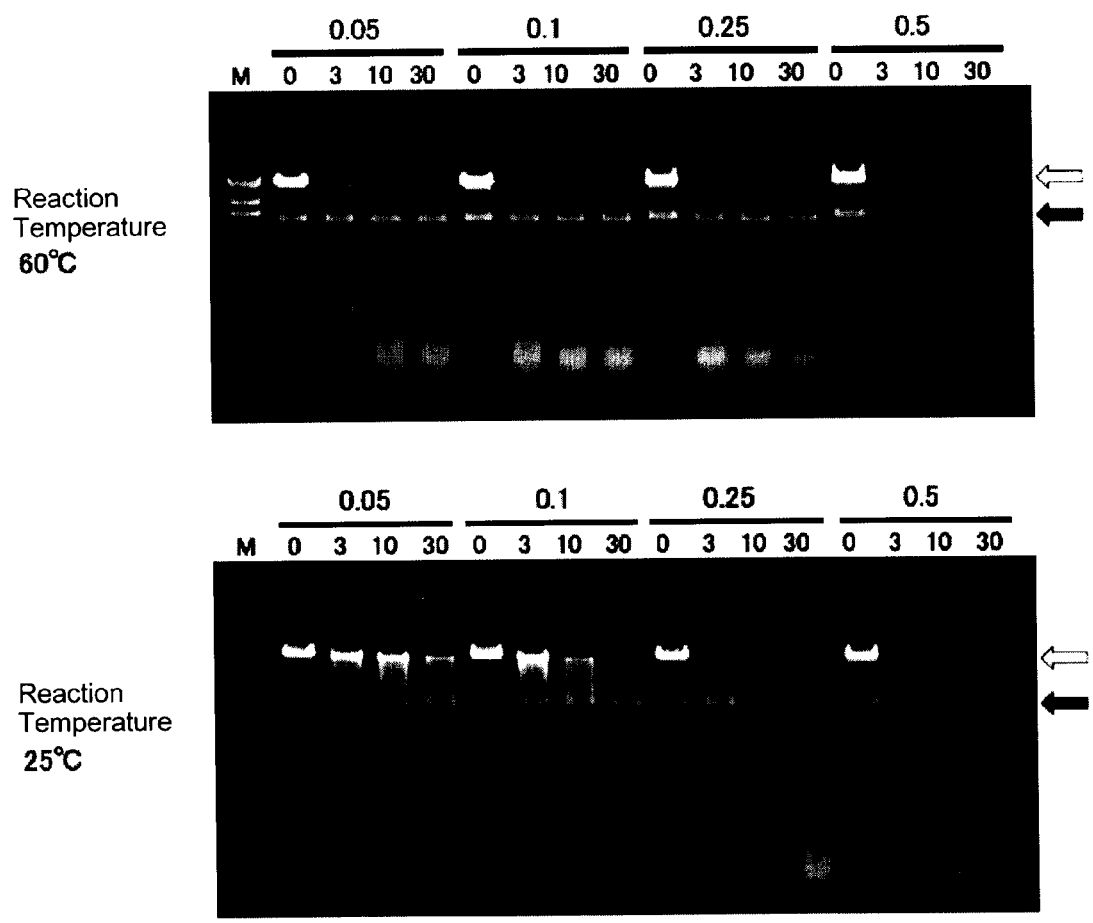
FIG. 10 is a figure showing influence of reaction temperature upon single-stranded DNA degradation of *Chionoecetes* (snow crab) DSN under a double-stranded DNA coexisting condition.

The thus obtained electrophoresis image is shown in FIG. 10. In FIG. 10, lane M is λ/Hind III digest DNA size marker (manufactured by TOYOBO), the numeral value on each lane represents the reaction time and the added amount of *Chionoecetes opilio* DSN purified enzyme is shown further thereon. In addition, the void arrow in FIG. 10 indicates position of the intact molecular weight of λ DNA, and the black arrow that of M13 DNA, respectively. As a result of this, complete disappearance of the band of single-stranded DNA was not found under all of the conditions tested even after a lapse of time of 30 minutes from the commencement of the reaction. On the other hand, the band of double-stranded DNA almost completely disappeared under all of the conditions tested, after a lapse of time of 30 minutes from the commencement of the reaction. This was a result equivalent to that of Example 5(2) that the *Chionoecetes opilio* DSN in the same amount of this Example (0.5 U) completely degraded a double-stranded DNA (λ DNA) by a reaction of merely 3 minutes (FIG. 5). Namely, it was found from the results of this Example that, as shown in FIG. 10, the *Chionoecetes opilio* DSN has a considerably low activity to degrade single-stranded DNA, or does not have the degradation activity, within a broad range of temperature of 25° C. and 60° C., and that this enzyme has a markedly high selectivity for double-stranded DNA. Additionally, it was found from a result of this Example that the *Chionoecetes opilio* DSN has more high double-stranded nucleic acid selectivity at a temperature of 25° C. or more and has further high double-stranded nucleic acid selectivity at 60° C.

EXAMPLE 10

RNA Degradation Activity of *Chionoecetes opilio* DSN

Figure 11:
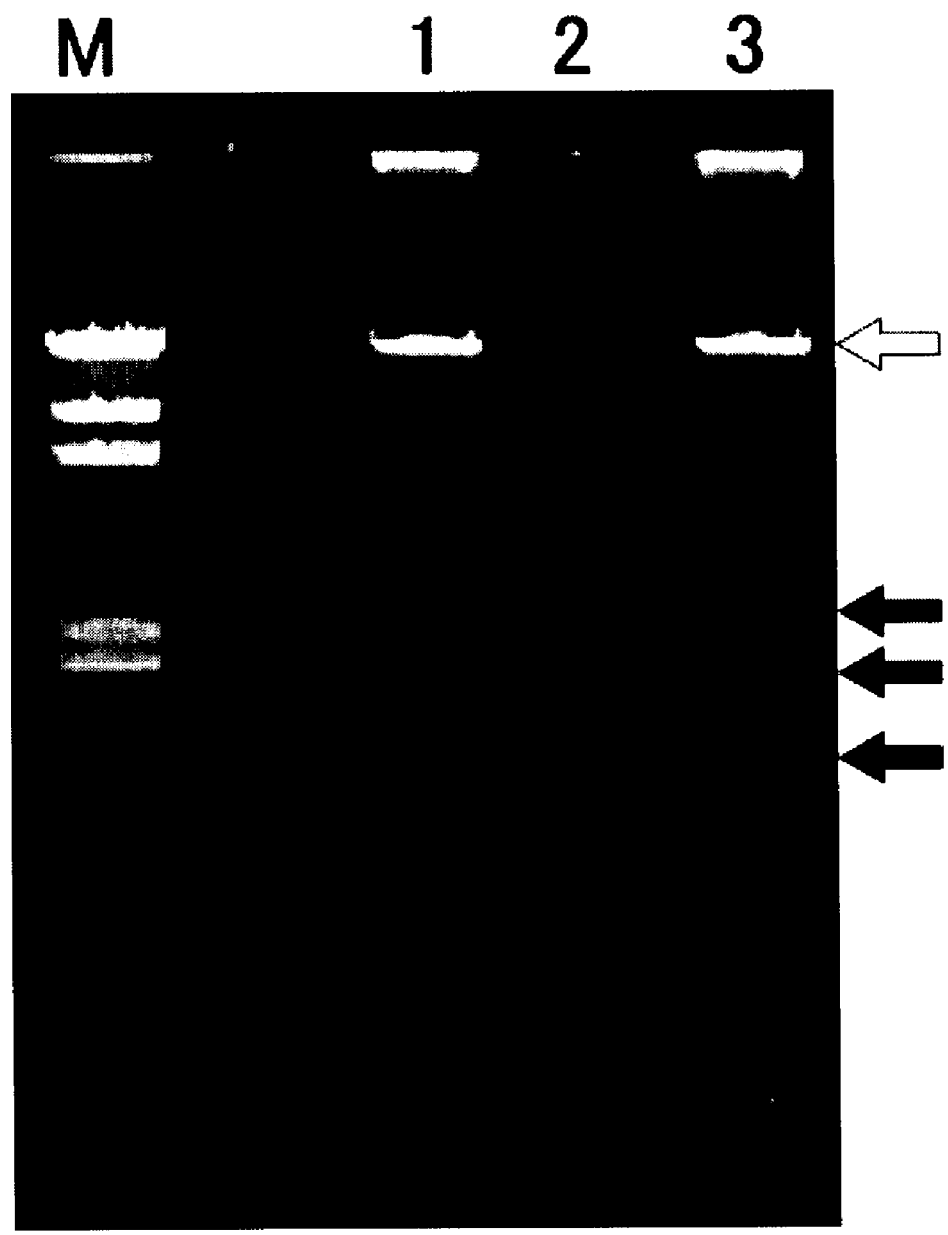
FIG. 11 is a figure showing RNA degradation activity of *Chionoecetes* (snow crab) DSN.

RNA degradation activity of *Chionoecetes opilio* DSN was evaluated. An insect cell-derived total RNA was used as the RNA substrate. The total RNA was extracted from $5\times10^6$ cells of the Sf9 cell using RNeasy Mini Kit (manufactured by QIAGEN). Procedure of the purification operation was carried out in accordance with the technical specification attached to said purification kit. From $5\times10^6$ cells of the Sf9 cell, 5.4 μg of total RNA was obtained. A λ DNA (manufactured by Nippon Gene) was used as the double-stranded DNA substrate, and the insect cell-derived total RNA prepared in the above was used as the RNA substrate. The substrate solution was prepared by adding 2%, DNA and total RNA to 40 mM Tris-HCl (pH 7.5), 8 mM $MgCl_2$ and 5 mM DTT, to be respective final concentrations of 10 μg/ml and 9 μg/ml. A reaction liquid was prepared by adding 1 μl (5 U) of the *Chionoecetes opilio* DSN purified enzyme to 9 μl of the substrate solution. Separately, a sample to which 1 μl of the buffer B of Example 4 was added instead of the enzyme was prepared as a negative control, and a sample to which 1 μl of a mixed liquid of RNase H and RNase T1, RNase mix (manufactured by Invitrogen), was added as a positive control. Each of the thus prepared reaction liquids was incubated at 60° C. for 3 minutes. After completion of the reaction, a 10 μl portion of the reaction liquid was subjected to 1.0% agarose gel electrophoresis. The gel was stained with SYBR Green II (manufactured by TAKARA BIO), and then the presence or absence and light or shade of respective substrate bands were compared under UV irradiation. The electrophoresis images are shown in FIG. 11. In FIG. 11, lane M is λ/Hind III digest DNA size marker (manufactured by TOYOBO). Lane 1 is a reaction liquid to which the RNase mix was added. Lane 2 is a reaction liquid to which the *Chionoecetes opilio* DSN purified enzyme was added, and lane 3 is a reaction liquid to which the buffer B of Example 4 was added.

As a result of this, in the case of the reaction liquid to which the *Chionoecetes opilio* DSN purified enzyme was added (FIG. 11, lane 2), the λ DNA as a double-stranded DNA substrate (void arrow) alone was degraded while the total RNA (black arrow) was not degraded. On the other hand, when the RNase mix was added instead of the enzyme (FIG. 11, lane 1), the total RNA (black arrow) alone was degraded while the λ DNA as a double-stranded DNA substrate (void arrow) was not degraded. Additionally, when the buffer B was added instead of the enzyme (FIG. 11, lane 3), both of the substrates were not degraded. It was shown from this result that the *Chionoecetes opilio* DSN does not degrade RNA but specifically degrades double-stranded DNA.

EXAMPLE 11

DNA-RNA Hybrid Chain Degrading Activity of *Chionoecetes opilio* DSN

Figure 12:
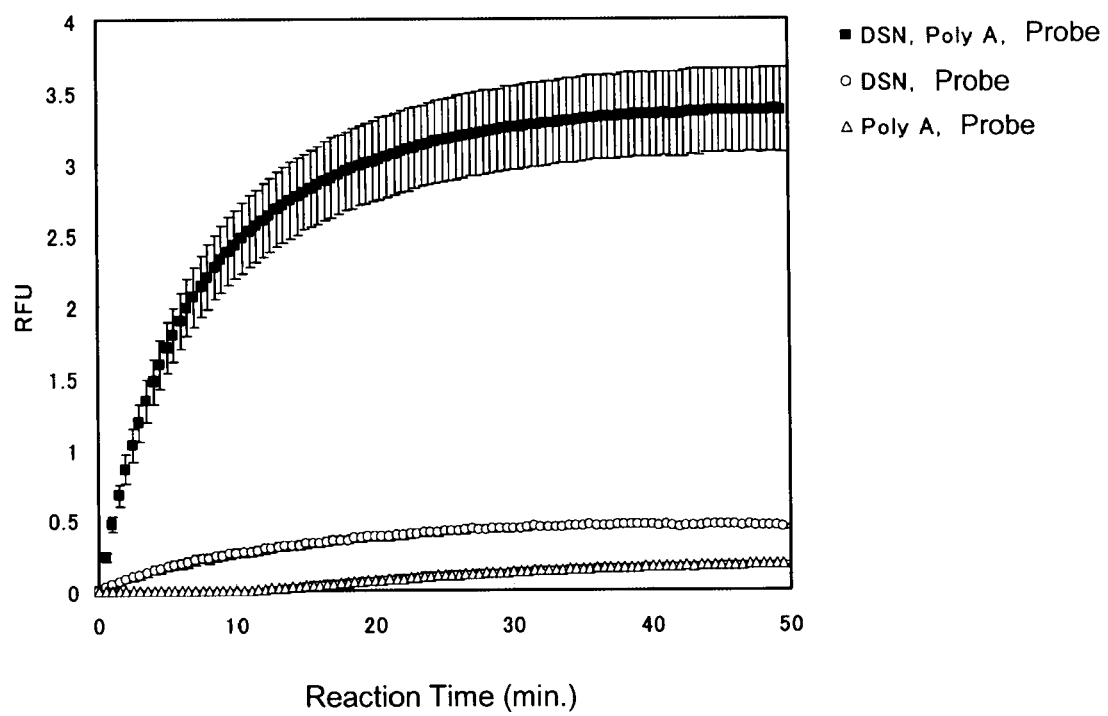
FIG. 12 is a figure showing DNA-RNA hybrid chain degradation activity of *Chionoecetes* (snow crab) DSN.

DNA-RNA hybrid chain degrading activity of the *Chionoecetes opilio* DSN was evaluated. In order to prepare a DNA- RNA hybrid chain, Poly A (manufactured by Roche) was used as the RNA chain, and an oligo DNA in which its 5' end was modified with FAM, and its 3' end with Eclipse Dark Quencher (Q), (5'-FAM-TTTTTTTTTTTTTTTTTTTTTTTT-Q-3') (SEQ ID NO:21) was used as the DNA chain. The substrate solution was prepared by adding Poly A and DNA probe to 40 mM Tris-HCl (pH 7.5), 8 mM $MgCl_2$ and 5 mM DTT, to be respective final concentrations of 12.5 nmol/ml and 0.5 nmol/ml. Separately, a substrate solution in which the DNA probe alone was added was also prepared. In order to prepare the DNA-RNA hybrid chain, hybridization was carried out by allowing the substrate solution to stand at room temperature for 30 minutes. Next, a reaction liquid was prepared by adding 1 μl (2.5 U) of the *Chionoecetes opilio* DSN purified enzyme to 19 μl of said substrate solution. Separately, a sample to which 1 μl of DCPC treated water was added instead of the enzyme was prepared as a negative control. By incubating the thus prepared reaction liquid at 37° C., the fluorescence value was measure at 30 second intervals, and the measurement was carried out for 50 minutes. The measurement of fluorescence value was carried out using DNA Engine Opticon System (manufactured by MJ Research). A result of the measurement is shown in FIG. 12. In a sample to which the Poly A, DNA probe and DSN were added, the relative fluorescence intensity (RFU) value was rapidly increased from just after commencement of the reaction. On the other hand, in a sample to which the DSN was not added and a sample to which the DSN and DNA probe alone were added, increased amount of the RFU value was markedly small in comparison with the sample to which the Poly A, DNA probe and DSN were added.

Figure 13:
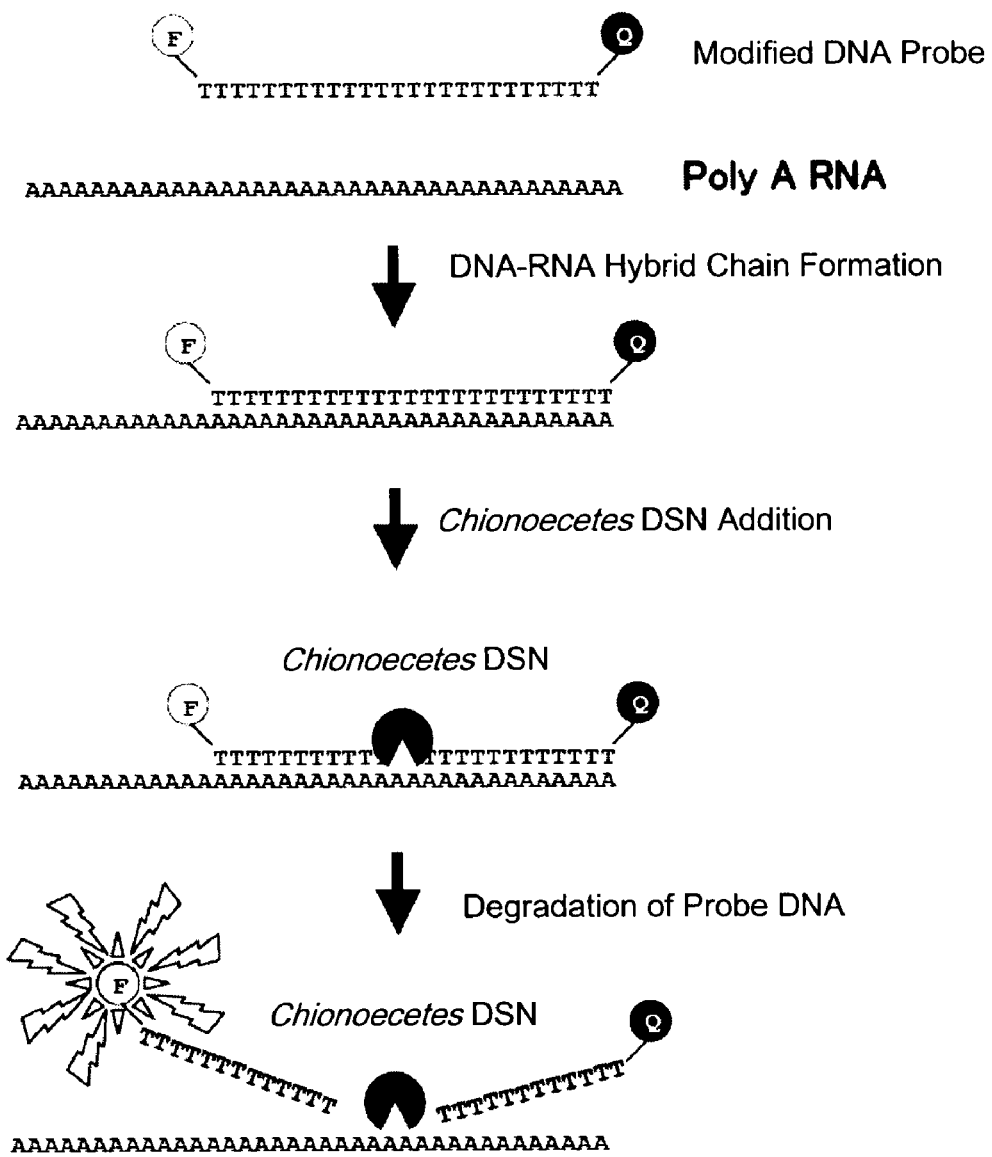
FIG. 13 is a schematic illustration representing DNA-RNA hybrid chain degradation by *Chionoecetes* (snow crab) DSN.

It was found from this result that, under such a condition that the Poly A and DNA probe can form a DNA-RNA hybrid chain, the *Chionoecetes opilio* DSN induced increase of fluorescence by degrading the DNA chain in said hybrid chain. A schematic view of this reaction is shown in FIG. 13. Additionally, it was shown also that, under such a condition that the DNA-RNA hybrid chain cannot be formed, namely when RNA is not present in the reaction system, the DNA probe is in the state of single chain and therefore can be hardly degraded by the *Chionoecetes opilio* DSN. Accordingly, it was shown that the *Chionoecetes opilio* DSN hardly shows degradation activity for the single-stranded DNA while specifically degrades the DNA chain in the DNA-RNA hybrid chain.

This Example also shows an example of the method for detecting the presence of an RNA in a sample using the *Chionoecetes opilio* DSN. Additionally, this Example shows an example of the method for specifically detecting an RNA which can form a DNA-RNA hybrid chain with a probe DNA using the *Chionoecetes opilio* DSN, namely it shows an example of the method for specifically detecting an RNA which has a nucleotide sequence complementary to a probe DNA.

[Sequence Listing Free Text]

SEQ ID NO:3: A nucleotide sequence of a primer based on a region preserved between crustacean-derived nuclease genes SEQ ID NO:4: A nucleotide sequence of a primer based on a region preserved between crustacean-derived nuclease genes SEQ ID NO:5: A nucleotide sequence of a primer based on a region preserved between crustacean-derived nuclease genes SEQ ID NO:6: A nucleotide sequence of a primer based on a region preserved between crustacean-derived nuclease genes SEQ ID NO:7: A nucleotide sequence of a primer based on a *Chionoecetes opilio* DSN gene internal sequence SEQ ID NO:8: A nucleotide sequence of a primer based on a *Chionoecetes opilio* DSN gene internal sequence SEQ ID NO:9: A nucleotide sequence of a primer based on a *Chionoecetes opilio* DSN gene internal sequence SEQ ID NO:10: A nucleotide sequence of a primer based on a *Chionoecetes opilio* DSN internal gene sequence SEQ ID NO:11: A nucleotide sequence of a primer based on a *Chionoecetes opilio* DSN internal gene sequence SEQ ID NO:12: A nucleotide sequence of a primer based on SEQ ID NO:20

SEQ ID NO:13: A nucleotide sequence of a primer based on SEQ ID NO:20

SEQ ID NO:14: A nucleotide sequence of an abridged universal amplification primer used in RACE method SEQ ID NO:15: A nucleotide sequence of an abridged anchor primer used in 5'-RACE method SEQ ID NO:16: A nucleotide sequence of an adaptor primer used in 3'-RACE method SEQ ID NO:17: An oligonucleotide sequence SEQ ID NO:18: A nucleotide sequence of a primer for inserting cDNA of SEQ ID NO:20 into an inset cell expression vector pVL1393

SEQ ID NO:19: A nucleotide sequence of a primer for inserting cDNA of SEQ ID NO:20 into an inset cell expression vector pVL1393

This patent application is based on Japanese Patent Application No. 2008-226389 filed on Sep. 3, 2008 and Japanese Patent Application No. 2009-131942 filed on Jun. 1, 2009 and the contents thereof are incorporated herein by reference.

What is claimed is:

1. An isolated and purified protein consisting of the amino acid sequence represented by SEQ ID NO:2 and having duplex-specific nuclease activity within a range of at least 55° C. to 63° C.

2. The protein of claim 1, which has duplex-specific nuclease activity within a range of at least 20° C. to 63° C.

3. The protein of claim 1, which has duplex-specific nuclease activity within a range of 20° C. to 63° C.

4. A reagent kit, which comprises at least one protein described in claim 1.

5. A method for producing a protein of claim 1, comprising transforming a host cell with a recombinant vector comprises a nucleic acid sequence encoding the protein in a medium, and
collecting the protein.

6. A method of degrading double-stranded DNA, comprising contacting a double-stranded DNA with an effective amount of the protein of claim 1 under conditions to degrade the double-stranded DNA.

7. A method of degrading DNA in a DNA-RNA hybrid duplex, comprising contacting a DNA-RNA hybrid duplex with an effective amount of the protein of claim 1 under conditions to degrade DNA of the DNA-RNA hybrid duplex.

8. An isolated and purified protein consisting of the amino acid sequence represented by SEQ ID NO:2 in which one or two amino acids are added, deleted, inserted or substituted, wherein the protein has duplex-specific nuclease activity within a range of at least 55° C. to 63° C.

9. The protein of claim 8, which is encoded by a nucleic acid sequence which hybridizes to SEQ ID NO: 1 under stringent conditions, wherein the stringent conditions comprises 6×SSC, 0.5% SDS, 5×Denhardt and 100 mg/ml of herring sperm DNA at 65° C. for 8 to 16 hours.

10. The peptide of claim 8, wherein the protein consisting of the amino acid sequence represented by SEQ ID NO:2 in which one or two amino acids are substituted.

11. The peptide of claim 8, wherein the protein consisting of the amino acid sequence represented by SEQ ID NO:2 in which one or two amino acids are added.

12. The peptide of claim 8, wherein the protein consisting of the amino acid sequence represented by SEQ ID NO:2 in which one or two amino acids are deleted.

13. The peptide of claim 8, wherein the protein consisting of the amino acid sequence represented by SEQ ID NO:2 in which one or two amino acids are inserted.

14. The protein of claim 8, which has duplex-specific nuclease activity within a range of at least 20° C. to 63° C.

15. The protein of claim 8, which has duplex-specific nuclease activity within a range of 20° C. to 63° C.

16. The protein of claim 8, which has a molecular weight by SDS polyacrylamide gel electrophoresis of from 42,000 to 46,000 and an isoelectric point of 4.4.

17. The protein of claim 8, which shows the duplex-specific nuclease activity in the presence of $Mg^{2+}$ ion or $Mn^{2+}$ ion and is insensitive to $Ca^{2+}$ ion.

18. The protein of claim 8, which is obtained from an organism belonging to Brachyura.

19. The protein of claim 8, which is obtained from the hepatopancreas of the genus *Chionoecetes*.

20. The protein of claim 8, which is obtained from *Chionoecetes opilio*.

21. A reagent kit, which comprises at least one protein described in claim 8.

22. A method for producing a protein of claim 8, comprising
transforming a host cell with a recombinant vector comprises a nucleic acid sequence encoding the protein in a medium, and
collecting the protein.

23. A method of degrading double-stranded DNA, comprising contacting a double-stranded DNA with an effective amount of the protein of claim 8 under conditions to degrade the double-stranded DNA.

24. A method of degrading DNA in a DNA-RNA hybrid duplex, comprising contacting a DNA-RNA hybrid duplex with an effective amount of the protein of claim 8 under conditions to degrade DNA of the DNA-RNA hybrid duplex.

* * * * *